United States Patent [19]
Brown et al.

[11] Patent Number: 6,140,051
[45] Date of Patent: Oct. 31, 2000

[54] FLUORESCENT DIBENZAZOLE DERIVATIVES AND METHODS RELATED THERETO

[75] Inventors: Lauren R. Brown, San Luis Obispo; Cheng Xu, San Mateo, both of Calif.

[73] Assignee: Promega Biosciences, Inc., Madison, Wis.

[21] Appl. No.: 09/118,220

[22] Filed: Jul. 17, 1998

Related U.S. Application Data

[60] Provisional application No. 60/053,339, Jul. 21, 1997.

[51] Int. Cl.$^7$ .................................................. C12Q 1/68
[52] U.S. Cl. ............................. 435/6; 435/7.1; 435/7.2; 436/501; 548/100; 548/122; 548/215; 548/217; 548/219; 548/335.1; 548/400; 548/407; 548/416
[58] Field of Search .................................. 548/100, 122, 548/215, 217, 219, 335.1, 400, 407, 416; 435/6, 7.1, 7.2; 436/501

[56] References Cited

U.S. PATENT DOCUMENTS

| | | | |
|---|---|---|---|
| 5,424,440 | 6/1995 | Klem et al. ............................. | 548/114 |
| 5,585,247 | 12/1996 | Habenstein .............................. | 435/18 |

FOREIGN PATENT DOCUMENTS

| | | |
|---|---|---|
| 0 399 409 | 11/1990 | European Pat. Off. . |
| WO 87/02667 | 5/1987 | WIPO . |
| WO 90/00618 | 1/1990 | WIPO . |
| WO 93/04077 | 3/1993 | WIPO . |
| WO 99/03849 | 1/1999 | WIPO . |

OTHER PUBLICATIONS

Bauman, et al., "A new method for fluorescence microscopical localization of specific DNA sequences by in situ hybridization of fluorochrome–labelled RNA" *Exp. Cell. Res.* 128:485–490 (1980).

(List continued on next page.)

*Primary Examiner*—Ardin H. Marschel
*Attorney, Agent, or Firm*—Michael Best & Friedrich LLP; Grady J. Frenchick, Esq.

[57] ABSTRACT

Dibenzazole compounds having the general structure:

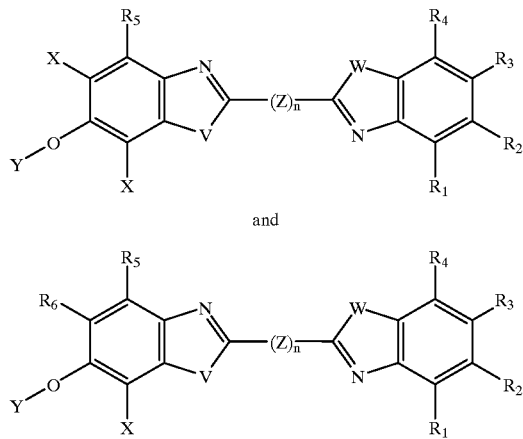

and wherein; $R_1$, $R_2$, $R_3$, $R_4$, $R_5$, $R_6$ are independently H or a substituent which aids in solubility of the compound or which provides a linker arm for linking the compound to another moiety; Y is H or a cleavable moiety; X is a hydrogen, halogen, $CF_3$, or $SO_3H$; V and W are oxygen or sulfur; Z is —C=C—, —C≡C— or an aromatic ring moiety; and n is 0, 1, or 2. When n=0 at least one of $R_1$, $R_2$, $R_3$, $R_4$, and $R_5$ is a substituent which aids in solubility of the compound or which provides a linker arm for linking the compound to another moiety or X is a halogen, $CF_3$ or $SO_3H$. These compounds are highly fluorescent and can be easily detected using a fluorometer. Derivatives in which the Y group is a substituent other than H contain a fluorescence inhibiting chemical moiety that upon removal restores the fluorescence of the compound. Methods for their synthesis and application are provided.

32 Claims, 9 Drawing Sheets

OTHER PUBLICATIONS

Cano, et al., "Evaluation of a Fluorescent DNA Hybridization Assay for the Detection of *Neisseria gonorrhoeae*", *Eur. J. Clin. Microbiol. Infect. Dis.* 11(7):602–609 (1992).

Fox, et al., "Fluorescence In Situ Hybridization: Powerful Molecular Tool for Cancer Prognosis", *Clin. Chem.* 41(11):1554–1559 (1995).

Gerald, et al., "Fluorometric detection of HIV–1 genome though use of an internal control, inosine–substituted primers, and microtiter plate format", *Clin. Chem.* 42(5):696–703, (1996).

Hosli, et al., "Quantitative Ultramicro–Scale Immunoenzymic Method for Measuring Ig Antigenic Determinants in Single Cells", *Clin. Chem.* 24(8):1325–1330, (1978).

Koster, et al., "Some Improvements of Polymer Oligodeoxynucleotide Synthesis", *Natural Products Chemistry, Elsevier, Amsterdam*, 227–237 (1984).

Moss, Donald, W., "Alkaline Phosphatase Isoenzymes", *Clin. Chem.* 28(10):207–2016, (1982).

Muller, et al., "Synthese von 2–Styryl–naphton[1,2–d]thiazolen", *J. Prakt. Chem.* 327(4):698–704, (1984).

Pastinen, et al., "Multiplex, fluorescent, solid–phase minisequencing for efficient screening of DNA sequence variation", *Clin. Chem.* 42(9):1391–1397, (1996).

Southwick, et al., "Cyanine Dye Labeling Reagents–Carboxymethylindocyanine Succinimidyl Esters", *Cytometry* 11:418–430, (1990).

Yolken, et al., "Enzyme–Linked Fluorescence Assay: Ultrasensitive Solid–Phase Assay for Detection of Human Rotavirus", *J. Clin. Microbiol.* 10(3):317–321, (1979).

CHEMICAL STRUCTURES OF DIBENZAZOLE COMPOUNDS WHEREIN N = 0

1a (FBBT):

1b (ClBBT):

1c (DiFBBT):

1d (BBTE):

1e (BBTES):

1f (BBTAA):

1h (ClBBTAA):

1i (BBTAAT):

1j (ClBBTP):

1k (BBTG):

1l (BBTAAG):

1m (BBTAATG):

1n (BBTESG):

1o (ProBBT):

1p (iBuBBT):

1q (HeptBBT):

1r (LauBBT):

1s (OleBBT):

1t (BBTEPA):

1u (BBTAASu):

1v (BBTEM):

1w (BBT Labeled Oligonucleotide or DNA):

Chemical Structures of Dibenzazole Compounds Where Z = -C=C- and N = 1

2a (BEBT):

2b (BEBTE):

2c (BEBTAA):

2d (BEBTES):

2e (BEBO):

2f (α-BENT):

2h (α-BENO):

2i (β-BENO):

2j (BEBTP):

2k (BEBTEG):

2l (BEBTESG):

Chemical Structures of Dibenzazole Compounds Where N = 1 and Z is -C≡C-.

FLUORESCENT DIBENZAZOLE DERIVATIVES AND METHODS RELATED THERETO

RELATED APPLICATION

This application claims priority under 35 U.S.C.§ 119(e) to U.S. Provisional Application Ser. No. 60/053,339, filed Jul. 21, 1997, abandoned.

FIELD OF THE INVENTION

This invention relates to the field of fluorescent compounds and fluorescent-based substrates and their use in the field of biological assays.

BACKGROUND OF THE INVENTION

Fluorescence is a property exhibited by certain chemicals that involves the excitation of the electronic state of the molecule through absorption of light of a given energy (wavelength), followed by a return to the ground state via certain electronic processes resulting in the emission of light of lower energy (longer wavelength). This property has been utilized for a variety of applications involving the high sensitivity detection of biological and other kinds of analytes.

One general application of this phenomenon is found in the use of artificial enzyme substrates, prepared by derivatizing a fluorescent compound (fluorophore) with a chemical moiety, to detect the presence of a corresponding enzyme. Successful applications require that the substrate (derivatized fluorophore) have a number of characteristics, including the following:

exhibit little or no background fluorescence from the unreacted substrate under the assay conditions;

be chemically stable under the variety of aqueous environments and pH ranges typically employed for the assay of the enzyme;

release a highly fluorescent product on reaction catalyzed by the target enzyme;

exhibit sufficient turn-over number (number of substrate molecules transformed per second per molecule of enzyme) to permit useful assay times;

have sufficient solubility in aqueous solution to allow zero-order kinetics to be achieved, thus permitting a direct correlation of the rate of reaction to the enzyme concentration; and exhibit linear kinetics over several orders of magnitude in the concentration of the enzyme (see overview in A. Lehninger, D. Nelson and M. Cox, *Principles of Biochemistry*, New York, Worth Publishers, 1993).

One example of the many enzymes that are measured quantitatively for the diagnosis of disease through the use of artificial substrates is alkaline phosphatase (ALP) EC3.1.3.1. Its presence is a valuable indicator of hepatobiliary disease (Mass, "Alkaline Phosphatase Isoenzymes," *Clin. Chem.* 28:2007–2016, 1982). ALP has also been measured to assess the completeness of milk pasteurization (Rocco, *Anal. Chem.*, 73(6):842–849).

Further, any analyte that can be directly related to the enzyme can also be detected. For example, an enzyme can be chemically conjugated to a polyclonal or monoclonal antibody targeted against a specific biological molecule present in a biological sample. Often the analyte in question is a protein or other chemical that is directly linked to a disease state. The general technique is referred to as Enzyme Immunoassay (EIA). An extensive review of EIA that utilizes fluorescence in particular is presented by Ilkka A. Hemmila in *Applications of Fluorescence in Immunoassays*, John Wiley & Sons, Inc., New York, 1991.

Several enzymes have found extensive use in fluorescence-based EIA applications, including alkaline phosphatase (R. H. Yolken and P. J. Stopa, *J Clin. Microbiol.* 10:317, 1979) and beta-D-galactosidase (Hosli et al., *Clin. Chem.* 24:1325, 1978). The driving force to utilize fluorescence-based EIA is the increase in sensitivity over colorimetric methods, as much as a 1000-fold improvement or more. Ishikawa et al., "Methods for Enzyme-labeling of Antigens, Antibodies, and Their Fragments," in T. T. Ngo, Ed., *Non-Isotopic Immunoassay*, Plenum Press, New York, 1988.

These same enzymes can also be attached to other molecules, such as DNA and RNA oligonucleotides and used in hybridization-based detection assays in which fluorescence again is generated. An example is the use of a fluorescent substrate (Attophos) to ALP (incorporated via an alkaline phosphatase-streptavidin conjugate) in the detection of *Neiseseria gonorrhoeae* by a hybridization technique (Cano et al., *Eur. J Clin. Microbiol. Infect. Dis.* 11(7):602–609, 1992). In another application, alkaline phosphatase is used in the detection of HIV-1 genome by Polymerase Chain Reaction (PCR) techniques, again via an alkaline phosphatase-streptavidin conjugate. (Gerard et al., "Fluorometric detection of HIV-1 genome through use of an internal control, inosine-substituted primers, and microtiter plate format," *Clinical Chemistry* 42(5):696–703 (1996)).

A second major application of fluorescent compounds is their use in directly labeling a component in a detection system. One important application is a technique known as Fluorescence In Situ Hybridization (FISH). Bauman et al., "A new method for fluorescence microscopical localization of specific DNA sequence by in situ hybridization of fluorochrome-labeled RNA," *Exp. Cell Res.* 138:485–90, 1980. In this technique a DNA or RNA probe against a specific genetic target is labeled with a fluorophore and is mixed with a sample. The presence of the target is detected when the probe hybridizes with the specific sequence, as revealed by the emission of the attached fluorescent label. Multi-target FISH can be achieved with the use of multiple fluorescent probes (Fox et al., "Fluorescence in situ hybridization: powerful molecular tool for cancer prognosis," *Clin. Chem.* 41(11):1554–1559, 1995).

Another application for direct-labeling is the use of fluorophore-labeled dideoxynucleotide triphosphates to prepare primers in conjunction with PCR techniques for use in DNA sequencing. In one typical application the fluorophore used was fluorescein (Pastinen et al., "Multiplex, fluorescent, solid-phase minisequencing for efficient screening of DNA sequence variation," *Clin. Chem.* 42(9):1391–1397, 1996).

The properties of a fluorophore, whether directly incorporated into a detection reagent or employed indirectly via an enzyme substrate, are critical to the achievement of high sensitivity and/or rapid analysis. Some of these properties have been summarized by Hemmila, supra, p. 109. These include:

high relative fluorescence: [ϵ×Q]>10,000, where ϵ is the molar absorptivity constant for the fluorophore and Q is the quantum yield (ratio of photons emitted to photons absorbed);

spectral resolution: large Stokes shift (difference between the wavelength of maximum excitation and the wavelength of maximum emission), thus avoiding background noise associated with the excitation beam of light;

photostability (to minimize the process of photo-bleaching); and ease of coupling and small size (to retain the reactivity of labeled reagents, such as antibodies or oligonucleotides).

There are additional properties that add significant value to the utility of a fluorophore(s) in particular applications, such as:

excitation wavelength near the output of lasers that have been introduced in recent years, one of the more widely used being the Argon 488 nm laser. Use of lasers, with their narrow-band output, substantially reduces background noise due to the excitation of a variety of other materials that may be present in a biological sample as compared to the use of a full spectrum lamp. Further, the laser's high intensity beam is able to pump more photons into a small volume, thus enhancing the sensitivity of the measurement by maximally exciting all available fluorophores. Both properties contribute to an increase in assay sensitivity;

fluorescent emission at longer wavelengths (>540) to reduce interfering background caused by other sources in the biological sample, including a strong Raman emission for water (605–635 nm), and endogenous fluorescent components in plasma and serum samples that extend up to 600 nm, with a particularly strong emission band from 430–540 nm for serum samples. Hemmila, *supra*, p. 63–6;

availability of multiple emission wavelengths through adjustments of structures;

presence of a moiety in the fluorophore that causes the level of fluorescence to be indicative of its environment (e.g., pH);

full development of fluorescence under physiological conditions (e.g., pH 6–8, etc.); and capability to adjust solubility of the fluorophore (low solubility for applications requiring precipitation; high solubility in applications involving homogeneous solution measurement).

Numerous fluorophores are known, many introduced in recent years, for use in a variety of applications. However, "the development of new fluorescent compounds with desired properties is hampered by the complexity of the fluorescence process. Currently available data are not sufficient to allow any definite generalizations in regard to the relationship between the molecular structure and fluorescence," Hemmila, *Applications of Fluorescence in Immunoassays*, John Wiley & Sons, Inc. 1991, volume 117, p.109. Guilbault supports Hemmila's conclusions and states "the electronic spectroscopy of large molecules is sufficiently complex that neither empirical generalizations nor more fundamental theoretical arguments are necessarily reliable to enable prediction of the fluorescence characteristics of complex molecules," Guilbault, *Practical Fluorescence*, Marcel Dekker, Inc., 2d ed., Revised and Expanded, 1990. It is, therefore, not surprising that a review of some representative fluorophores currently available reveal significant shortcomings in one or more of the preferred properties, as shown in the following discussion 4-Methylumbelliferone (4-MU) is one of the oldest fluorophores in use as an enzyme substrate (Yolken and Stopa, *supra*). Its fluorescent properties include $\lambda_{EX}$ of 367 nm, $\lambda_{EM}$ of 449 nm, and a Stokes Shift of 82 nm ($\lambda_{EX}$ and $\lambda_{EM}$ represent the wavelength of maximum excitation and emission, respectively). Unfortunately, its $\lambda_{EM}$ is too short to avoid significant interference from background interference in biological samples, there is no means for converting it to a direct label, it cannot be excited efficiently by Argon 488 line and its efficient excitation with UV light requires expensive quartz optics.

Fluorescein is a widely used fluorophore with a $\lambda_{EX}$ of 492 nm and a $\lambda_{EM}$ of 520 nm (Stokes Shift of 28 nm). Hemmila, supra, p112. Fluorescein has a high quantum yield and is excited efficiently by Argon laser, but the Stokes Shift is quite small. Further the $\lambda_{EM}$ is too short to avoid some background interference in typical biological samples and there no functionality on the fluorescein molecule that can be used to solubilize galactoside and similar substrate derivatives to render such derivatives really of practical utility. Finally, fluorescein is known to be quite photo-labile, making it a difficult fluorophore to use in many applications.

Rhodamine (as TRITC) is a widely used fluorophore with a $\lambda_{EX}$ of 540 nm and a $\lambda_{EM}$ of 575 nm (Stokes Shift of 35 nm). Hemmila, supra. Its emission wavelength is longer than most background sources, but its Stokes Shift also is quite small. Further, it has no functional group that can be denivatized for enzyme substrate preparation.

Cy2, a cyanine dye introduced in recent years (Southwick et al., *Cytometry II*:418, 1990) has a $\lambda_{EX}$ of 489 nm and a $\lambda_{EM}$ of 506 nm (Stokes Shift 18 nm). The $\lambda_{EM}$ of this fluorophore is optimal for use with the Argon laser, but the Stokes Shift is extremely small. Further, Cy2 has no moiety for converting the fluorophore to an enzyme substrate.

2'-(2-Benzothiazolyl)-6'-hydroxy-benzothiazole (BBT) has a $\lambda_{EX}$ of 419 nm and a $\lambda_{EM}$ of 561 nm with the Stokes Shift being 142 nm (U.S. Pat. No. 5,424,440, hereby incorporated by reference). BBT, a dibenzothiazole derivative, has several desirable properties as a fluorophore. It has an exceptionally large Stokes shift (142 nm) and has a moiety (phenolic hydroxyl group) that serves as a handle for conversion to enzyme substrates, such as the phosphate (AttoPhos®, JBL Scientific, Inc., San Luis Obispo, Calif.). However, this material has a number of significant shortcomings. First, the $\lambda_{EX}$ is too short to be maximally excited by an Argon 488 nm laser. Second, the $\lambda_{EM}$ is long enough (561 nm) to be above the most intense background fluorescence present in serum samples but is still too short to be above some of the weaker background interference in a band from 540 to 580 nm, as described in Hemmila (*supra*, p.65). Third, derivatives of BBT that could serve as substrates specific for several important enzymes, such as galactosidase, esterases, and lipases are not of practical value because of quite limited solubility of the resulting compounds (e.g., much less than 1 mM solubility for the galactoside of BBT, making zero order kinetics impossible to achieve over a wide range of concentrations of enzyme). Fourth, BBT is a suitable fluorophore for use as an alkaline phosphatase derivative (AttoPhos®) since its pKa is 8.5 and is fully ionized and therefore fully fluorescent at the pH typically employed for ALP assay (pH 10.3). However, the assay for many enzymes, such as beta-D-galactosidase, esterases and lipases, is preferably performed in the pH range of 6.0 to 8.0. In this pH range BBT is only partially ionized and, therefore, much less intensely fluorescent. This is a further barrier to the use of BBT in this type of application. Fifth, there is no means by which BBT can be used as a direct label, since the only functional group available is the phenolic hydroxyl moiety, the derivatization of which prevents the fluorescence at 560 nm. Finally, BBT is a fluorophore introduced with the choice of only one wavelength and no indication of how additional wavelengths might be achieved. There are several interesting applications, involving simultaneous detection of two or more targets, which require the availability of two or more fluorophores.

2-Phenyl-6-hydroxybenzoxazole (Habenstein, U.S. Pat. No. 5,585,247) has a $\lambda_{EX}$ of 370 nm and a $\lambda_{EM}$ of 460 nm with Stokes Shift being 110 nm. This is a benzoxazole derivative that also has a larger than usual Stokes shift (110 nm), but it is optimally excited by UV light, not an Argon laser. The emission is not long enough to avoid the interfering background fluorescence of typical biological samples. Further, there are no means indicated to affect solubility nor the dependence of fluorescence on pH. Derivatives prepared from this fluorophore thus have limited practical usefulness as substrates for such applications as measurement of lipase, esterase and glycolytic enzymes. Further, there is no means by which this fluorophore might be utilized as a direct label.

SUMMARY OF THE INVENTION

In one aspect of the present invention fluorescent dibenzazole compounds (benzothiazole and benzoxazole) are provided having the structure:

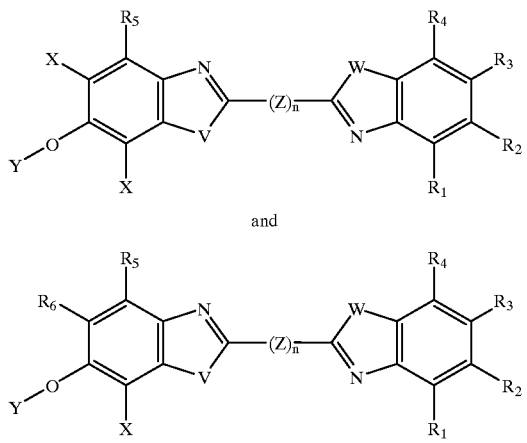

and wherein;

$R_1$, $R_2$, $R_3$, $R_4$, $R_5$ and $R_6$ are independently —H or substituents which aid in solubility of the compound or which provides a linker arm for linking the compound to another moiety;

Y is H or a cleavable moiety;

X is independently hydrogen, halogen, —$CF_3$, or —$SO_3H$;

V and W are independently oxygen or sulfur;

Z is —C=C—, —C≡C—, or a aromatic ring moiety; and n is 0, 1, or 2.

Preferably, when n=0 at least one of $R_1$, $R_2$, $R_3$, $R_4$, and $R_5$ is a substituent which aids in solubility of the compound or which provides a linker arm for linking the compound to another moiety and/or X is halogen, —$CF_3$, or —$SO_3H$.

In particular, $R_1$, $R_2$, $R_3$, $R_4$, $R_5$, or $R_6$ may be independently H or a substituent which aids solubility such as, for example —$SO_3$, —$CO_2$, or —$PO_4^{-2}$. In the case where the substituent which aids solubility is —$PO_4^{-2}$, Y is preferably not phosphoryl. In one preferred embodiment $R_1$ and $R_2$, or $R_2$ and $R_3$, or $R_3$ and $R_4$ together form an aromatic ring such as benzene or naphthalene. In another preferred embodiment, at least one of $R_1$, $R_2$, $R_3$, $R_4$ and $R_5$ is —$CH_2CH_2SO_3H$. In another preferred embodiment, $R_5$ is hydrogen.

In another preferred embodiment, at least one of $R_1$, $R_2$, $R_3$ and $R_4$ is a linker arm of the formula —$(CH_2)_n$—$R_{10}$ wherein n is a number selected from 0, 1, 2, 3, 4 and 5, and is independently selected at each occurrence, and $R_{10}$ is selected from —OH, —$SO_3H$, —COOH, —C(=O)NH$(CH_2)_mR_{11}$, —O—P(OCH$_2$CH$_2$CN)(N(R$_9$)$_2$),

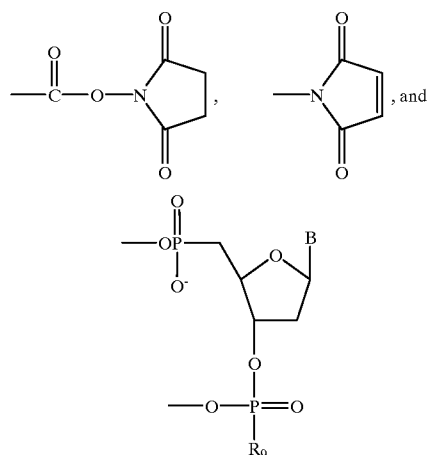

wherein $R_{11}$ is selected from —OH, $SO_3H$ and —COOH, m is a number selected from 1, 2, 3, 4 and 5, $R_9$ is a $C_1$–$C_6$ alkyl group and B represents a purine or pyrimidine moiety, each variable being independently selected at each occurrence.

Y may be —H, a phosphoryl such as —$PO_3H_2$, a glycosyl moiety such as for example galactosyl, glucosyl, or glucoronoyl, a long chain fatty acid of about 12 to about 24 carbon atoms such as $R_8$—C(=O)— wherein $R_8$ is a straight chain or branched alkyl or alkenyl group of 12 to about 24 carbon atoms; preferably a straight chain or branched alkyl or alkenyl group of about 16 to about 24 carbon atoms; most preferably a straight chain or branched alkyl or alkenyl group of about 16 to about 20 carbon atoms such as oleoyl, or a short chain fatty acid of 1 to about 12 carbon atoms such as $R_7$—C(=O)— wherein $R_7$ is a straight chain or branched alkyl or alkenyl group of 1 to about 10 carbon atoms such as lauroyl and heptanoyl or preferably is a straight chain or branched alkyl or alkylene group of 1 to about 5 carbon atoms such as propionyl and iso-butyryl.

Particular preferred dibenzazole compounds include those having the structures provided in FIGS. 1 and 2.

The invention also comprises applications of the new fluorescent compounds.

DETAILED DESCRIPTION OF THE PREFERRED EMBODIMENT

Figure 1A:
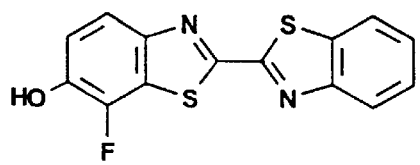
FIGS. 1A–1C: show representative chemical structures of dibenzazole compounds where n=0.
Figure 1A:
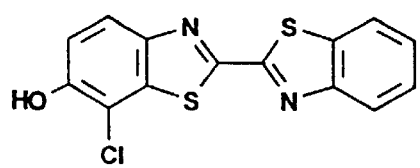
Figure 1A:
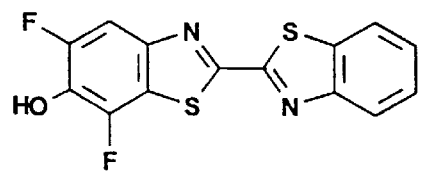
Figure 1A:
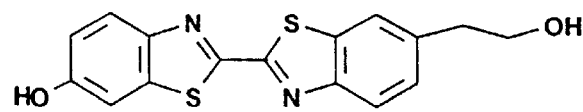
Figure 1A:
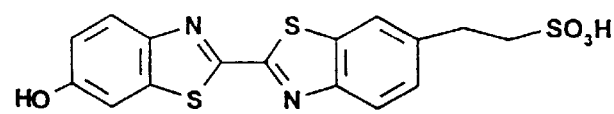
Figure 1A:
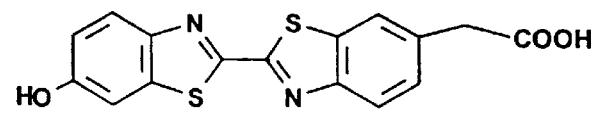
Figure 1A:
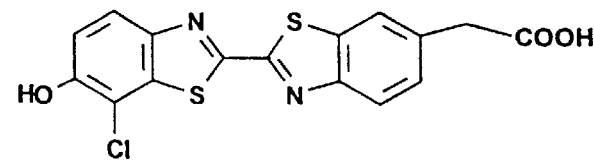
Figure 1A:
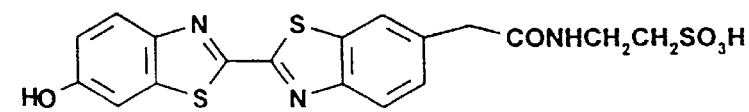

To assist in understanding the specification the following definitions of terms used herein are provided and are to have the meaning proscribed unless otherwise stated:

"Sample" as used herein referes to an aliquot of liquid removed from a biological source, such as but not limited to blood, blood serum, blood plasma, urine, cells, cell extracts or an aliquot of a liquid obtained from a non-biological source, such as but not limited to, a product of a chemical reaction or a chemical that has been conjugated to or complexed with biologically derived materials such as enzymes and antibodies.

"Agent" as used herein refers to a component of a sample that is the target of analysis, such as but not limited to a protein, a DNA sequence, a RNA sequence, a product of a chemical reaction, or a chemical that has been conjugated to or complexed with biologically derived materials such as enzymes and antibodies.

"Biopolymer" as used herein refers to a substance of high molecular weight consisting of a sequence of linked biochemical units such as but not limited to peptides, oligopeptides, polypeptides or proteins which consist of linked amino acid biochemical units, oligonucleotides, polynucleotides which consist of linked deoxyribonucleotides or ribonucleotides and oligosaccharides and polysaccharides which consist of linked sugar molecules.

"Polymer" as used herein refers to a substance of high molecular weight consisting of multiple linked chemical units, including for example nylon, polyvinylidene difluoride and polystyrene.

"Inorganic matrix" as used herein refers to a solid surface of inorganic chemical composition, including but not limited to silicon, silicon dioxide and alumina, that can be derivatized with an agent.

"Cleavable Moiety" as used herein is a chemical unit that can be separated from the fluorophore by enzymatic or non-enzymatic hydrolysis.

"Aromatic ring moiety" as used herein means a cyclic structure capable of extending electron resonance delocalization of the benzazole ring, such as benzene, pyrrole, pyridine, furan and thiophene.

"Linker arm" as used herein means a chain of two or more atoms that provides a means to chemically attach the compounds of the invention to another compound such as an enzyme, an antibody, an oligonucleotide, a polymer, biopolymer or inorganic matrix.

"Glycosyl" as used herein means a mono- or oligosaccharide moiety capable of being attached to the compounds of the invention via an O-glycosidic bond.

"Fluorophore" as used herein means a chemical moiety that can be induced to emit light of one wavelength when excited by light of a different wavelength.

Synthesis of Fluorophores

Fluorophores provided in the present invention can be represented by the general formula:

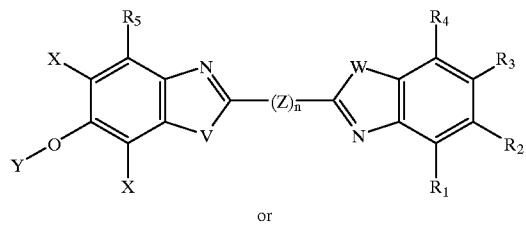

or

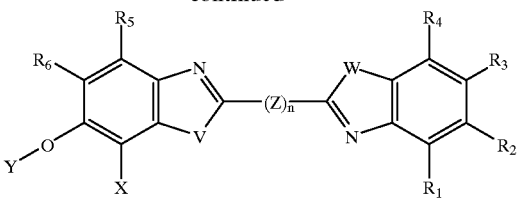

wherein, $R_1$, $R_2$, $R_3$, $R_4$, $R_5$, and $R_6$ are independently —H, a substituent which aids in solubility of the compound, or a linker arm for linking the compound to another moiety;

Y is —H or a cleavable moiety;

X is independently hydrogen, halogen, —$CF_3$, or —$SO_3H$;

V and W are independently oxygen or sulfur;

Z is —C=C—, —C≡C— or an aromatic moiety; and n is 0, 1, or 2.

Preferably, when n=0 at least one of $R_1$, $R_2$, $R_3$, $R_4$, and $R_5$ is a substituent which aids in solubility of the compound or which provides a linker arm for linking the compound to another moiety and/or X is halogen, —$CF_3$, or —$SO_3H$.

X, which may be the same or different, is either —H or an electronegative substituent such as a halogen for example —F, —Cl, —Br, —I, or —$CF_3$, or —$SO_3H$, which aids in lowering the pKa of the phenolic hydroxyl group.

One embodiment of the present invention provides fluorophores which are derivatized BBT or HBO (6-hydroxybenzoxazole) compounds. These derivatized BBT and HBO compounds are structurally new and either have distinct fluorescent properties and/or have new uses. For example, when X is —Cl or —F, the halogenated compounds fully fluoresce at a much lower pH (7–8) than BBT itself (pH 9–10). This characteristic of full fluorescence at lower pH (7–8) is desirable for many biological assays.

When one of the R substituents, preferably $R_2$, is a functionalized moiety ("linker arm") such as an alkyl phosphoramidite or a carboxylic N-hydroxysuccinimide ester, the resulting BBT derivative can be used for direct oligonucleotide labeling or for direct protein labeling. Preparation of the BBT and HBO derivatives described herein is meant to illustrative and not limiting.

The halogenated BBT compounds can be prepared either by direct halogenation of BBT using sulfuryl chloride by the chemistry generally well-known to one skilled in the art or by first halogenating the intermediate 2-cyano-6-hydroxybenzothiazole and then coupling with 2-aminothiophenol using the procedure reported in U.S. Pat. No. 5,424,440.

The BBT derivative having a $R_1$, $R_2$, $R_3$, $R_4$, or $R_5$ substituent is synthesized from a substituted 2-aminothiophenol. Condensation of the substituted 2-aminothiophenol with 2-cyano-6-hydroxybenzothiazole affords the substituted BBT.

Table 1 lists representative BBT fluorophore derivatives of the present invention and their fluorescent properties according to the formula:

TABLE 1*

[Structure: two benzothiazoles joined at 2-position; left ring has O at 6-position and X at 7-position; right ring has R at 6-position]

| Compound | X | R | $\lambda_{EX}$ (nm) | $\lambda_{EM}$ (nm) | Stokes Shift (nm) |
|---|---|---|---|---|---|
| BBTE | H | CH$_2$CH$_2$OH | 422 | 550 | 128 |
| BBTAA | H | CH$_2$COOH | 430 | 549 | 119 |
| BBTAAT | H | CH$_2$CONHCH$_2$CH$_2$SO$_3$H | 430 | 548 | 118 |
| FBBT | F | H | 423 | 552 | 129 |
| ClBBT | Cl | H | 435 | 550 | 115 |
| ClBBTAA | Cl | CH$_2$COOH | 437 | 545 | 108 |
| SBBT | SO$_3$H | H | 420 | 538 | 118 |

* The fluorescence is measured at pH about 10 in AttoPhos buffer (JBL Scientific, San Luis Obispo, CA).

Another embodiment of the present invention provides fluorophores which are composed of two benzazoles joined by —C=C— or —C≡C— at their 2-position as shown in the general structure, wherein n is 1, and V and W are —S or O. Surprisingly, these derivatives exhibit excitation maxima only about 30–40 nm higher than BBT, but the emission maxima are as much as 65 mu longer than the $\lambda_{EM}$ of BBT. While the $\lambda_{EX}$ for this family of fluorophores is slightly less than the Argon laser line of 488 nm, the actual preferred excitation wavelength for such fluorophores in the presence of their corresponding substrate derivatives is a slightly longer wavelength than 440 nm in order to avoid interfering background fluorescence from unreacted substrate. Thus, this structural modification unexpectedly produced fluorophores that are nearly ideal for excitation by the Argon 488 nm line. Further, the Stokes Shift of this family of fluorophores are exceptionally large and the emission is greater than 580 nm, as preferred, some being as large as 624 nm. Table 2 lists some preferred fluorophores of this series of the present invention and their fluorescent properties.

TABLE 2*

| Compound | Structure | $\lambda_{EX}$ (nm) | $\lambda_{EM}$ (nm) | Stokes Shift (nm) |
|---|---|---|---|---|
| BEBT | [HO-benzothiazole—CH=CH—benzothiazole] | 440 | 620 | 180 |
| BEBO | [HO-benzothiazole—CH=CH—benzoxazole] | 438 | 604 | 166 |
| α-BENT | [HO-benzothiazole—CH=CH—naphtho[2,1]thiazole] | 443 | 624 | 181 |
| α-BENO | [HO-benzothiazole—CH=CH—naphtho[2,1]oxazole] | 432 | 585 | 153 |
| β-BENO | [HO-benzothiazole—CH=CH—naphtho[1,2]oxazole] | 443 | 602 | 159 |

* The fluorescence is measured at pH about 10 in AttoPhos buffer (JBL Scientific, San Luis Obispo, CA).

Another embodiment of the present invention provides fluorophores which are composed of two benzazoles joined by a aromatic moiety at their 2-position as shown in the general structure, wherein n is 1, and V and W are —S or —O. A variety of aromatic moieties may join the two benzazoles preferably the aromatic moiety is benzene, pyrrole, pyridine, furan or thiophene. Another embodiment of the present invention provides fluorophores which are composed of two benzazoles joined by an aromatic moiety at their 2-position as shown in the general structure, wherein n is 1, and V and W are —S or —O. A variety of aromatic moieties may join the two benzazoles, in which the aromatic moiety preferably is benzene, pyrrole, pyridine, furan or thiophene. The synthesis of these compounds is approached by the step-wise condensation of the aromatic moiety substituted with two cyano- groups (or one cyano- group and one synthon convertible subsequently to a cyano- group) and the appropropriate aminothiophenol(s). For example,

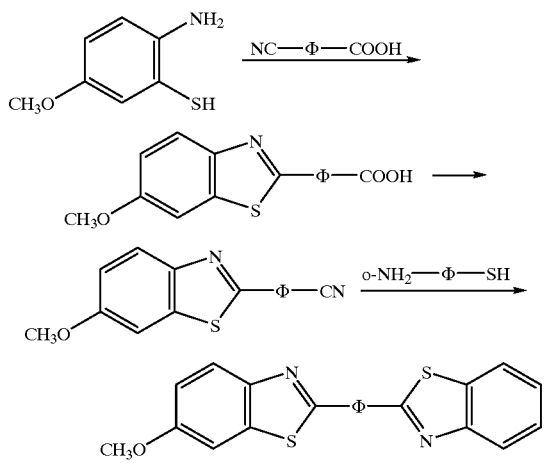

where Φ is a benzene, pyrrole, pyridine, furan or thiophene moiety. In these examples of the claimed compounds the excitation can be achieved with the Argon 488 nm light, with the Stokes shift also being sizable (100–160 nm) and the emission occurring at long wavelengths (600–660) nm.

The synthesis of this series of fluorophores starts from 6-methoxybenzothiazole-2-aldehyde which can be made by reducing 2-cyano-6-methoxybenzothiazole using lithium trialkoxyaluminum hydride by a method described by Sandler and Karo in Organic Functional Group Preparations, 2nd Ed., 189, (1983), Academic Press. The benzothiazole aldehyde reacts with 2-methylbenzothiazole under ZnCl$_2$ catalysis to form 2'-(2-benzothiazolylethenyl)-6'-methoxybenzothiazole, Muller et al., *J Prakt. Chem.* 327:698–704, 1985. After demethylation with trimethylsilyl iodide or boron tribromide, 2'-(2-benzothiazolylethenyl)-6'-hydroxybenzothiazole (BEBT) is obtained.

If the 2-methylbenzothiazole is replaced with 2-methylbenzoxazole in the above preparation, the final product will be 2'-(2-benzoxazolylethenyl)-6'-hydroxybenzothiazole (BEBO). All other compounds listed in Table 2 can be prepared using similar chemistry by one skilled in the art.

Synthesis of Enzyme Substrates

Although all the compounds of the invention having enzymatically cleavable moieties, i.e., "enzymatic substrates" are generated by blocking the phenolic hydroxyl group of the fluorophores described above, enzymatic substrates for different enzymes require different chemistry for their preparation, as described below.

Phosphatase substrates are prepared by phosphorylation of the phenolic OH of fluorophores with dimethylchlorophosphate, followed by demethylation of the resulting dimethylphosphate ester using trimethylsilyl bromide (U.S. Pat. No. 5,424,440).

Glycosides of the fluorophores as substrates for carbohydrate hydrolases in this invention are prepared by coupling a fluorophore with a bromo-sugar using well known Koenigs-Knorr chemistry.

Esterase and lipase substrates of this invention are carboxylic acid esters and can be conveniently prepared by reacting a fluorophore with the corresponding acyl chloride in the presence of an organic tertiary amine.

Synthesis of Direct Labeling Fluorophores

The fluorophore compounds of the present invention which can be used for direct oligonucleotide and DNA labeling, i.e., "direct labeling fluorophores", have so-called "linker arms" to conjugate the fluorophore compounds directly to the oligonucleotide. Such compounds can be prepared from the corresponding alkyl alcohol derivative via phosphoramidite chemistry, Koster et al. in Natural Products Chemistry, Elsevier, Amsterdam, 227–237, 1984.

The N-hydroxysuccinimide esters of carboxylic acid derivatives of the fluorophores of the current invention are prepared by coupling the acid with N-hydroxysuccinimide. These esters can be used for direct protein labeling.

pH Dependence of Fluorescence

Figure 3:
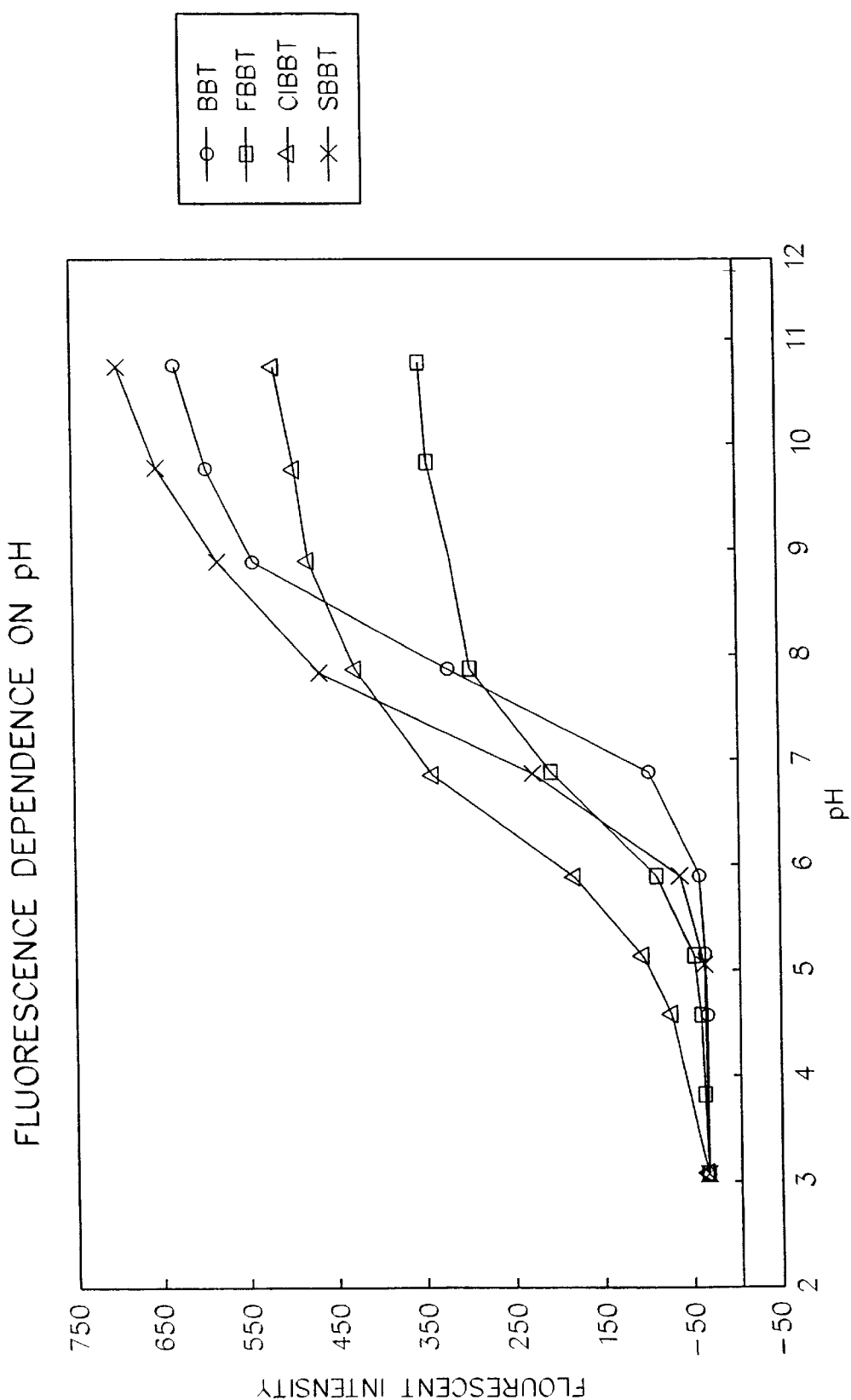
FIG. 3 illustrates the fluorescence dependence on pH.

To make the phenolic fluorophore fully fluorescent at a lower pH (7–8) to achieve the best performance for some enzymatic and biological assays, some fluorophores are synthesized with electronegative substituent(s), e.g., chloride, bromide, iodide, fluoride, trifluoromethyl, —SO$_3$H, etc. These substituted derivatives may be analyzed at different pH's for their fluorescent efficiency. The dependence of fluorescent intensity on pH for some preferred compounds of the invention, and comparative compounds, are shown in FIG. 3. Compared to the unsubstituted compound, BBT (also shown in the graph, U.S. Pat. No. 5,424,440), the electronegatively substituted BBT derivatives, especially CIBBT, can reach their maximum fluorescence at a pH very close to physiological conditions (pH 7–8). The pH dependent characteristic change of fluorescent intensity of these fluorophores can also find applications as pH titration fluorescent indicators.

Uses

In another aspect of the invention, methods are provided for detecting an agent in a biological sample using the dibenzazole compounds described above comprising; adding a compound to a biological sample and detecting the hydrolysis of the compound by fluorescence. Examples of such uses, include detection of enzymes in biological samples, detection of antibodies to specific analytes conjugated with appropriate enzymes (Enzyme ImmunoAssays), detection of protein, DNA or RNA samples labeled directly or indirectly with enzymes using gels and membranes for separation and visualization. Further, non-biological samples with conjugated enzymes can also be detected using the appropriate substrate incorporating the dibenzazole compounds described herein.

In addition, methods of conjugating the above compounds directly to a molecule comprising, linking a linker arm to one or more of positions $R_1$, $R_2$, $R_3$, or $R_4$, and conjugating to the linker a functional group that will bind to the molecule are also provided. Such a conjugating target molecule includes an oligonucleotide, a DNA, an amino compound, a peptide, a protein, a polymer, and a bio-polymer.

Accordingly, the present invention provides the following advantages:

Fluorescent compounds, which, upon attachment of a chemical moiety, have little or no fluorescence at the wavelength of assay but, upon removal of the chemical moiety with appropriate enzymatic action, are strongly fluorescent.

Fluorescent compounds and their derivatives which maintain stability in a variety of aqueous environments.

Fluorescent compounds and their derivatives which have solubility characteristics suitable for the various applications.

Fluorescent compounds which may be used at a variety of pH ranges.

Fluorescent compounds which are easily detectable above background interference.

Fluorescent compounds which exhibit large Stokes' shifts.

Fluorescent compounds which have $\lambda_{EX}$ that can be used efficiently by the Argon laser 488 nm line.

Fluorescent compounds that have $\lambda_{EM}$ >540 nm and preferably >580 nm.

Fluorescent compounds and their derivatives which can be used for direct labeling applications.

Fluorescent compounds and their derivatives which can be used as fluorescent acid-base indicators.

The following examples are provided by way of illustration and not by way of limitation.

In the following examples, NMR data were measured by a Bruker AC-300 300 MHz instrument; mass spectra were obtained on a VG Platform, Fisons Instruments; fluorescence data were obtained from a Perkin Elmer Luminescence Spectrometer, Model LS50B.

EXAMPLE 1

Synthesis of BEBTP

Synthesis of 6-Methoxybenzothiazole-2-aldehyde: 2-Cyano-6-methoxybenzothiazole (10.0 g, 52.6 mmol) was suspended in a mixture of anhydrous ether (400 ml) and 2-propanol (36 ml). The suspension was cooled to about −30° C. by a dry-ice bath. Lithium aluminum hydride (7.0 g, 184.5 mmol) was added slowly while keeping the reaction temperature below −30° C. under argon atmosphere. The reaction mixture was stirred for 1 hr after the addition of lithium aluminum hydride and then poured slowly into a mixture of 2 N sulfuric acid (900 ml) and ethyl acetate (500 ml). After stirring for 10 min the organic layer was separated and the aqueous layer was extracted with ethyl acetate (200 ml). The combined organic phase was washed with water (200 ml) and then dried with anhydrous sodium sulfate (50 g) overnight. The dried solution was concentrated and then flash chromatographed on silica gel to give 3.1 g (30.5%) of a yellowish solid.

$^1$H NMR (300 MHz, CDCl$_3$): δ 10.10 (1H, s, CHO), 8.10 (1H, d, J=9.3 Hz), 7.38 (1H, d, J=2.6 Hz), 7.22 (1H, dd, J$_1$=2.3; J$_2$=9.0), 3.93 (3H, s).

MS: m/z 193 (M$^+$).

Synthesis of 2'-(2-Benzothiazolylethenyl)-6'-methoxybenzothiazole: A mixture of 6-Methoxybenzothiazole-2-aldehyde (1.0 g, 5.2 mmol), 2-methylbenzothiazole (5 ml) and zinc chloride (1.0 g) was heated at 180° C. under argon for 10 min and then cooled down to room temperature. Methanol (30 ml) was added. After stirring for 10 min, the resulting precipitate was filtered, washed with methanol, and then dried. Yield: 0.95 g (81%).

$^1$H NMR (300 MHz, CDCl$_3$): δ 8.04 (1H, d, J=8.07 Hz), 7.93 (1H, d, J=9.54 Hz), 7.88 (1H, d, 8.07 Hz), 7.78 (1H, d, 16.17), 7.70 (1H, d, 15.45 Hz), 7.46 (2H, m), 7.32 (1H, d, 2.22 Hz), 7.10 (1H, dd, J$_1$=8.82 Hz; J$_2$=2.94 Hz), 3.89 (3H, s).

MS: m/z 324 (M$^+$).

Synthesis of 2'-(2-Benzothiazolylethenyl)-6'-hydroxybenzothiazole: 2'-(2-Benzothiazolyl-ethenyl)-6'-methoxybenzothiazole (1.0 g, 3.1 mmol) was dissolved in chloroform (10 ml). Boron tribromide (1.3 ml) was added. The reaction mixture was stirred at room temperature for 4 hr and then diluted with heptane (20 ml). The precipitate was filtered, washed with 5% ammonium hydroxide aqueous solution, and then dried. Yield: 0.6 g (62%).

$^1$H NMR (300 MHz, DMSO-d$_6$): δ 8.16 (1H, d, J=8.07 Hz), 8.05 (1H, d, J=8.07), 7.87 (1H, d, J=8.82), 7.87 (1H, d, J=15.42 Hz), 7.78 (1H, d, J=16.17 Hz), 7.53 (2H, m), 7.43 (1H, d, J=2.94 Hz), 7.02 (1H, dd, J$_1$=8.82 Hz; J$_2$=2.22 Hz).

MS: m/z 310 (M$^+$), 309 ((M$^-$).

Synthesis of 2'-(2-Benzothiazolylethenyl)-6'-hydroxybenzothiazole dimethylphosphate: 2'-(2-Benzothiazolylethenyl)-6'-hydroxybenzothiazole (1.12 g, 3.6 mmol) was suspended in THF (40 ml) and potassium tert-butoxide (0.81 g, 7.2 mmol) was added. After the mixture was stirred at room temperature for 40 min, dimethylchlorophosphate (0.45 ml, 0.6 g, 4.2 mmol) was added dropwise. The reaction mixture was stirred at room temperature for 2 hr and then poured into heptane (300 ml). The resulting precipitate was collected, washed with heptane and dried. Yield: 1.46 g (96%). Further purification by flash silica gel chromatography gave a yellowish solid.

$^1$H NMR (300 MHz, CDCl$_3$): δ 8.07 (1H, d, J=7.35 Hz), 8.00 (1H, d, J=8.82 Hz), 7.91 (1H, d, J=7.35 Hz), 7.80 (1H, m), 7.78 (2H, m), 7.45 (2H, m), 7.36 (1H, m), 3.91 (6H, d).

MS: m/z 418 (M$^+$).

Figure 2A:
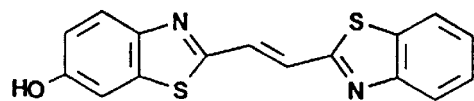
FIGS. 2A–2B show representative chemical structures of dibenzazole compounds where Z=—C=C— and n=1.
Figure 2A:
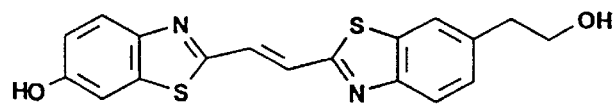
Figure 2A:
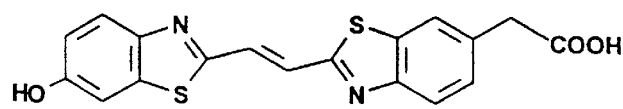
Figure 2A:
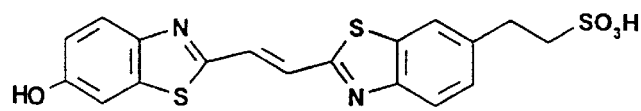
Figure 2A:
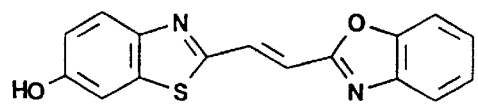
Figure 2A:
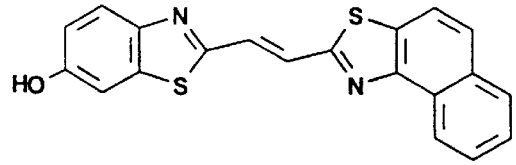
Figure 2A:
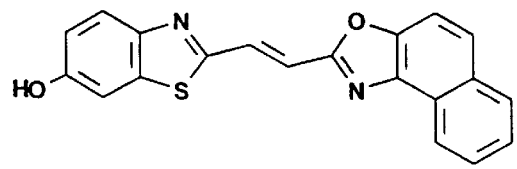
Figure 2A:
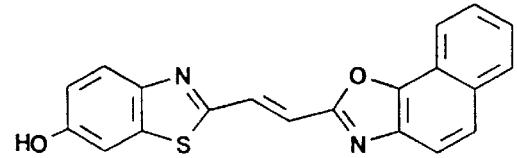

Synthesis of 2'-(2-Benzothiazolylethenyl)-6'-hydroxybenzothiazole phosphate di(2-amino-2-methyl 1,3-propanediol) salt (FIG. 2j-acid form): 2'-(2-Benzothiazolylethenyl)-6'-hydroxybenzothiazole dimethylphosphate (0.5 g, 1.2 mmol) was suspended in dioxane (10 ml). To the suspension trimethylsilyl bromide (0.5 ml) was added. The reaction mixture was stirred at 70–80° C. for 1.5 hr. More trimethylsilyl bromide (0.25 ml) was added. After stirring at the same conditions for additional 30 min, the reaction mixture was poured into a solution composed of 2-amino-2-methyl 1,3-propanediol (0.75 g) and ethanol (20 ml). After stirring for 10 min the mixture was cooled in a refrigerator overnight. The resulting precipitate was filtered, washed with ethanol three times, and dried. Yield: 0.64 g (89%).

$^1$H NMR (300 MHz, D$_2$O): δ 7.31 (1H, s), 7.26 (1H, d, J=8.82 Hz), 7.13 (2H, m), 6.88 (1H, m), 6.78 (2H, m), 6.67 (2H, m), 3.41(8H, m), 0.98 (6H, m).

MS: m/z 389 ((M−1)$^-$).

EXAMPLE 2

Synthesis of BEBTESG

Synthesis of 4-Acetamidophenethyl Acetate: 4-Aminophenethyl alcohol (10.0 g, 72.9 mmol) was dissolved in DMF (100 ml). Acetic anhydride (35 ml, 37.9 g, 37.1 mmol) and triethylamine (100 ml, 72.6 g, 71.7 mmol) were added. The reaction mixture was stirred at room temperature for 2 hr. Water (50 ml) was added to decompose the excess acetic anhydride. After stirring for 10 min the reaction solution was concentrated to remove the solvents. The residue was treated with water (400 ml) to precipitate the desired product. The precipitate was filtered, washed with water, and dried in vacuum. Yield: 8.2 g (51%).

t), 2.01 (3H, s), 1.97 (3H, s).

Synthesis of 4-Thioacetamidophenethyl Acetate: 4-Acetamidophenethyl acetate (10.0 g, 45.2 mmol) and phosphorus pentasulfide (10.0 g, 22.5 mmol) were suspended in toluene (200 ml). The suspension was refluxed for 40 min. After cooling the supernatant was decanted into a separatory funnel and washed with 50% aqueous $Na_2CO_3$ solution (70 ml) and then with water (70 ml). The organic toluene layer was dried over anhydrous sodium sulfate overnight. The dried toluene solution was concentrated to dryness to give a yellowish solid (7.6 g, 71%). This solid was used for next reaction without further purification.

Synthesis of 2-Methyl-6-acetoxyethylbenzothiazole: $K_3Fe(CN)_6$ (7.6 g, 23.1 mmol) was dissolved in water (18 ml) and then mixed with 50 ml 2% NaOH aqueous solution. 4-Thioacetamidophenethyl acetate (1.0 g, 4.1 mmol) was dissolved in dichloromethane (50 ml) and then added to the $K_3Fe(CN)_6$ solution. The reaction mixture was stirred at room temperature for 1 hr. The organic layer was separated by a separatory funnel, washed with water, and then dried over anhydrous sodium sulfate. The dried solution was concentrated and then purified by flash silica gel chromatography. Yield: 0.6 g (61%).

$^1$H NMR (300 MHz, $CDCl_3$): δ 7.82 (1H, d), 7.62 (1H, d), 7.24 (1H, dd), 4.27 (2H, t), 2.99 (1H, t), 2.77 (3H, s), 1.99 (3H, s).

Synthesis of 2'-((6-Acetoxyethyl-2-benzothiazolyl) ethenyl)-6'-methoxybenzothiazole: 6-Methoxybenzothiazole-2-aldehyde (500 mg, 2.6 mmol) and 2-methyl-6-acetoxyethylbenzothiazole (530 mg, 2.3 mmol) were dissolved in a mixture of acetic anhydride (4 ml) and acetic acid (1 ml). The reaction solution was refluxed overnight. After cooling to room temperature, the reaction solution was first mixed with methyl t-butyl ether (5 ml) and then with heptane (10 ml). The resulting precipitate was collected, washed with heptane, and dried under vacuum. Yield: 0.6 g (65%).

$^1$H NMR (300 MHz, $CDCl_3$): δ 7.91 (1H, d), 7.87 (1H, d), 7.72–7.59 (3H, m), 7.32–7.27 (2H, m), 7.05 (1H, dd), 4.29 (2H, t), 3.84 (3H, s), 3.02 (2H, t), 1.99 (3H, s).4

MS: m/z 411 ($M^+$).

Figure 2B:
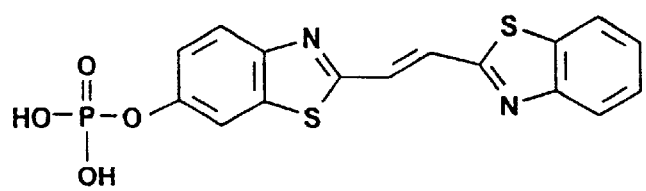
Figure 2B:
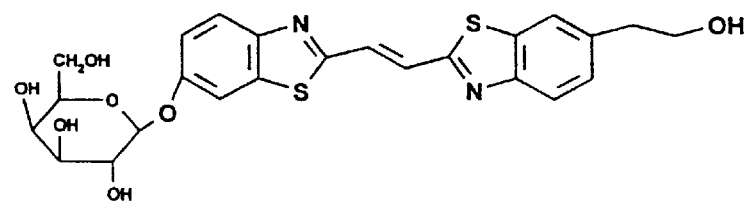
Figure 2B:
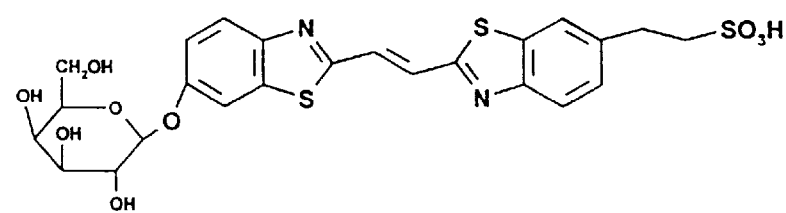

Synthesis of 2'-((6-Hydroxyethyl-2-benzothiazolyl) ethenyl)-6'-hydroxybenzothiazole (FIG. 2b): 2'-((6-Acetoxyethyl-2-benzothiazolyl)ethenyl)-6'-methoxybenzothiazole (4.7 g, 11.0 mmol) was mixed with 1 M $BBr_3$ dichloromethane solution (40 ml, 40.0 mmol) and the reaction mixture was stirred at room temperature for 4 hr. Heptane (120 ml) was added and the mixture was stirred for 10 min. The resulting precipitate was filtered, washed with heptane, and dried under vacuum. The dried solid was suspended in water (50 ml) and the pH of the suspension was adjusted with concentrated $NH_4OH$ to 7–8. The solid was collected by filtration, washed with water twice, and then redissolved in methanol (150 ml). The methanol solution was mixed with 6 N NaOH (10 ml) and then stirred at room temperature for 3.5 hr. After addition of water (500 ml) the reaction mixture was neutralized with 6 N HCl to pH 5. The resulting precipitate was collected, washed with water, and dried in vacuum. Yield: 2.9 g (76%).

MS: m/z 354 ($M^+$).

Synthesis of 2'-((6-Bromoethyl-2-benzothiazolyl) ethenyl)-6'-hydroxybenzothiazole: 2'-((6-Hydroxyethyl-2-benzothiazolyl)ethenyl)-6'-hydroxybenzothiazole (1.0 g, 2.8 mmol) was suspended in concentrated hydrobromic acid (20 ml). The suspension was refluxed for 8 hr and then neutralized with concentrated $NH_4OH$ to pH 7–8. The precipitate was collected, washed with water, and dried in vacuum. Yield: 1.1 g (93%).

MS: m/z 416 and 418 ($M^+$).

Synthesis of 2'-((6-Sulfoethyl-2-benzothiazolyl)ethenyl)-6'-hydroxybenzothiazole β-D-Galactoside (FIG. 21): 2'-((6-Bromoethyl-2-benzothiazolyl)ethenyl)-6'-hydroxybenzothiazole (1.0 g, 2.4 mmol) was suspended in saturated sodium hydrogensulfite aqueous solution (25 ml) and tetrabutylammonium hydrogen sulfate (0.5 g, 1.5 mmol) was added. The reaction mixture was refluxed for 1 hr and then cooled to room temperature. The supernatant was decanted and the remaining precipitate was washed with water. The precipitate was suspended in water (30 ml). The pH of the suspension was adjusted with 1 N NaOH to 10. After stirring for 30 min, the solution was filtered and the filtrate was neutralized with acetic acid to pH 5–6. The neutralized solution was concentrated to about 20 ml and then combined with 1 N NaOH (40 ml) and dichloromethane (40 ml). α-D-Tetraacetylgalactosyl bromide (2.0 g, 4.8 mmol) and tetrabutylammonium hydrogen sulfate (0.5 g) were added. The reaction mixture was vigorously stirred at room temperature overnight. The organic layer was separated and purified by silica gel chromatography to afford 2'-((6-sulfoethyl-2-benzothiazolyl)ethenyl)-6'-hydroxybenzothiazole β-D-tetraacetylgalactoside (140 mg). The tetraacetylgalactoside was deprotected by 25% sodium methoxide (3 ml) in THF (15 ml) at room temperature. The reaction mixture was neutralized with acetic acid to pH 6–7 and then concentrated to dryness. The residue was purified by C18 reverse phase column chromatography to give a yellowish solid (36 mg).

MS: m/z 580 ($M^-$).

EXAMPLE 3

Synthesis of BBT Carboxylic Acid Esters

Synthesis of 2'-(2-Benzothiazolyl)-6'-hydroxybenzothiazole Propionate (FIG. 10): 2'-(2-Benzothiazolyl)-6'-hydroxybenzothiazole (0.5 g, 1.7 mmol) was suspended in THF (20 ml). To the suspension were added diisopropylethylamine (2 ml) and propionyl chloride (0.4 g, 0.4 ml, 4.6 mmol). The reaction mixture was stirred at room temperature for 30 min and then refluxed for 1 hr. The reaction solution was concentrated to dryness. Water (10 ml) was added. The resulting precipitate was collected by filtration and washed with water two times. The product was dried in vacuum. Yield: 0.5 g (83%).

$^1$H NMR (300 MHz, $CDCl_3$): δ 8.16 (1H, d,), 8.14 (1H, d), 7.99 (1H, d), 7.75 (1H, d), 7.53 (2H, m), 7.29 (1H, dd), 2.66 (2H, q), 1.30 (3H, t).

MS: m/z 340 ($M^+$).

Synthesis of 2'-(2-Benzothiazolyl)-6'-hydroxybenzothiazole Oleate (FIG. 1s): 2'-(2-Benzothiazolyl)-6'-hydroxybenzothiazole (1.0 g, 3.5 mmol) was suspended in THF (10 ml). To the suspension were added diisopropylethylamine (4 ml) and oleoyl chloride (3.9 g, 4.3 ml, 13 mmol). The reaction mixture was stirred at 50–60° C. for 2 hr. The formed precipitate was removed by filtration. The filtrate was concentrated to remove the solvent. The oil residue was stirred with 200 ml 0.5 M sodium carbonate aqueous solution for 10 min. The resulting precipitate was collected by filtration and washed with 0.5 M sodium carbonate, with water, and finally with methanol. The product was dried in vacuum. The crude product was recrystallized from THF and methanol. Yield: 1.1 g (58%).

$^1$H NMR (300 MHz, CDCl$_3$): δ 8.16 (1H, d,), 8.14 (1H, d), 7.99 (1H, d), 7.75 (1H, d), 7.53 (2H, m), 7.28 (1H, dd), 5.36 (2H, m), 2.62 (2H, t), 2.03 (4H, m), 1.79 (2H, m), 1.31 (26H, m), 0.88 (3H, t).

MS: m/z 548 (M$^+$).

EXAMPLE 4

Synthesis of BBTE

Synthesis of 2'-(6-Hydroxyethylbenzothiazol-2-yl))-6'-hydroxybenzothiazole (FIG. 1d): 4-Aminophenethanol (60.0 g, 440.0 mmol) and ammonium thiocyanate (67.0 g, 880 mmol) were dissolved in glacial acetic acid (600 ml). The solution was cooled with an ice-bath down to 0–10° C. Bromine (70.0 g, 440.0 mmol) was dissolved in acetic acid (100 ml) and then added dropwise through an addition funnel into the above cooled solution in 1 hr. The reaction mixture was stirred at about 10° C. for additional 35 min. The formed precipitate was filtered and redissolved in water (200 ml). The filtrate was concentrated to dryness and the residue was also redissolved in water (1000 ml). The two aqueous solutions were combined and neutralized with concentrated ammonium hydroxide to pH 8. The resulting precipitate was collected and dried in vacuum.

The dried material was dissolved in a KOH aqueous solution (213.8 g KOH in 480 ml water). The solution was refluxed for 80 min and then cooled to room temperature. The reaction solution was diluted with 450 ml water and then neutralized with acetic acid to pH 6. This solution was further diluted with water (1300 ml). 2-Cyano-6-hydroxybenzothiazole (23.4 g, 130 mmol) was dissolved in methanol (960 ml) and added all at once to the diluted aqueous solution. The resulting yellow precipitate was filtered, washed with water and then with methanol, and dried in vacuum. Yield: 36.6 g (84%).

MS: m/z 328 (M$^+$).

EXAMPLE 5

Synthesis of BBTEPA

Synthesis of 2'-(6-Acetoxybenzothiazol-2-yl)-6'-benzothiazolylethyl alcohol: 2'-(6-Hydroxybenzothiazol-2-yl)-6'-benzothiazolylethyl alcohol (1.0 g, 3.0 mmol) was dissolved in 10 ml of anhydrous pyridine and co-evaporated under full vacuum. The flask was released under argon and the contents dissolved in 20 ml of anhydrous pyridine and the flask then sealed with a rubber stopper. The solution was treated all at once with 4,4'-dimethoxytrityl chloride (1.0 g, 3.0 mmol) and stirred magnetically at room temperature overnight. The reaction mix was checked the next morning by HPLC and contained mostly the desired mono-DMT. The reaction mix was then cooled in a IPA/H20 dry ice bath and acetyl chloride (320 μl, 4.5 mmol) was added dropwise to it. The reaction mix was removed from the ice bath and allowed to warm to room temperature and continued stirring for 1.5 hr after which time an HPLC showed the reaction to be complete. The reaction mix was then concentrated on a rotoevaporator to dryness and triturated with 50 ml of acetonitrile. The light yellow solids were collected and rinsed with acetonitrile. The solids were then dissolved in 20 ml of dichloromethane (DCM) and with magnetic stirring treated with 15 ml of 0.2M benzenesulfonic acid in 7:3 DCM:MeOH. After 15 minutes, the reaction mix was quenched with triethylamine (5 ml) and promptly stored at –15° C. overnight to facilitate crystallization. The crystals were collected the next morning and rinsed with DCM then vacuum dried giving a final weight of 0.52 g (45%) of light tan solids.

$^1$H NMR (300 MHz, DMSO-D$_6$): δ 8.21 (1H, d, J=8.8 Hz), 8.10 (3H, m), 7.52 (1H, d, J=9.1 Hz), 7.42 (1H, d=6.9 Hz), 3.71 (2H, t, J=6.7 Hz), 2.92 (2H, t, J=6.7 Hz), 2.35 (3H, s, CH$_3$CO).

Synthesis of 2'-(6-Acetoxybenzothiazol-2-yl)-6'-benzothiazolylethyl phosphoramidite (1t):

2'-(6-Acetoxybenzothiazol-2-yl)-6'-benzothiazolylethyl alcohol (0.5 g, 1.3 mmol) was co-evaporated with anhydrous pyridine (10 ml) then released from the vacuum with argon. The dry solids were suspended in 10 ml of DCM then treated with triethylamine (450 μl). With magnetic stirring, 2'-cyanoethyl-N,N-diisopropylaminochlorophosphoramidite (0.33 g, 1.5 mmol) was added dropwise and the reaction was stirred at room temperature for 2 hr. The reaction mix was then concentrated to a thick yellow oil, taken up in a minimum volume of DCM, and purified on silica gel with 2:1 ethyl acetate:heptane with 2% triethylamine to give 0.41 g (55%) of a light yellow solid (single spot on TLC).

$^1$H NMR (300 MHz, CDCl$_3$): δ 8.15 (1H, d, J=8.9 Hz), 8.06 (1H, d, J=8.5 Hz), 7.85 (1H, d, J=1.1 Hz), 7.74 (1H, d, J=2.2), 7.43 (1H, m) 7.28 (1H, m), 3.75 (6H, m), 3.09 (2H, d, J=13.3 Hz), 2.59 (2H, d, J=12.8 Hz), 2.36 (3H, s), 1.14 (12H, m) $^{31}$p NMR (300 MHz, CDCl$_3$, PO$_4$ STD.) δ 147.45 (s).

EXAMPLE 6

Synthesis of BBTAASu

Synthesis of 2'-(6-Hydroxybenzothiazol-2-yl)-benzothiazole-6'-acetic acid (FIG. 1f): 4-Aminophenylacetic acid (5.0 g, 33.0 mmol) and ammonium thiocyanate (5.0, 66.0 mmol) were dissolved in glacial acetic acid (50 ml). The solution was cooled with an ice-bath down to 0–10° C. Bromine (5.3 g, 33.0 mmol) was dissolved in acetic acid (8 ml) and then added dropwise through an addition funnel into the above cooled solution in 20 min. The reaction mixture was stirred at about 10° C. for additional 45 min. The formed precipitate was filtered, rinsed with ethyl acetate, and dried in vacuum. The dried material was dissolved in a KOH aqueous solution (26.9 g KOH in 60 ml water). The solution was refluxed for 2 hr and then cooled to room temperature. The reaction solution was diluted with 15 ml water and then neutralized with acetic acid to pH 6. 2-Cyano-6-hydroxybenzothiazole (2.5 g, 14 mmol) was dissolved in methanol (100 ml) and added all at once to the neutralized reaction solution. The reaction mixture was stirred for 1 hr and then allowed to stand at room temperature overnight. The resulting yellow precipitate was filtered, washed with acetone, dried in vacuum. Yield: 4.0 g (82%).

$^1$H NMR (300 MHz, DMSO-d$_6$): δ 7.88 (1H, d, J=8.46 Hz), 7.83 (1H, s), 7.77 (1H, d, J=9.18), 7.44 (1H, dd, J$_1$=8.46 Hz; J$_2$=1.47 Hz), 7.10 (1H, d, J=2.19 Hz), 6.95 (1H, dd, J$_1$8.82 Hz; J$_2$p2.19 Hz), 3.42 (2H, s).

MS: m/z 341 (M$^-$).

Synthesis of 2'-(6-Hydroxybenzothiazol-2-yl)-benzothiazole-6'-acetic acid N-Hydroxysu ceinimide Ester (FIG. 1u): 2'-(2-Hydroxybenzothiazolyl)-benzothiazole-6-acetic acid (1.0 g, 3.0 mmol) and N-hydroxysuccinimide (0.7 g, 6.0 mmol) were dissolved in DMF (20 ml). Carbonyldmidazole (4.0 g, 24 mmol) was added. The reaction

EXAMPLE 7

CLBBT Synthesis

2'-(Benzothiazol-2-yl)-7'-chloro-6'-hydroxybenzothiazole (FIG. 1b): To a suspension of finely powdered BBT (10.0 g, 35.2 mmol) in dichloromethane (1 L) in a 3-L three-necked round-bottomed flask fitted with a reflux condenser was added sulfiiryl chloride (21.2 ml, 263.8 mmol) all at once via graduated cylinder. The resulting orange suspension was brought to reflux under an argon atmosphere for 12 hr. Addition sulfuryl chloride (10.0 ml, 124.5 Hzmol) was added to the reaction mixture and reflux was continued for another 12 hr. The reaction mixture was cooled to room temperature and poured onto ice-water (ca. 500 ml). The yellow precipitate was isolated by filtration. The yellow solid material was air-dried and then dried under vacuum overnight to afford 4.0 g (36%) of the title compound.

$^1$H NMR (300 MHz, $CD_3OD$, DMSO-$d_6$) δ 8.08 (m, 2H), 7.88 (d, J=7.88 Hz, 1H), 7.55 (m, 2H), 7.22 (d, J=8.8 Hz, 1H).

MS m/z 317 (M-H).

7-Chloro-2-fyano-6-hydroxybenzothiazole. To a suspension of 2-cyano-6-hydroxybenzothiazole (1.0 g, 5.7 mmol) in dichloromethane (100 ml) in a 250-ml round-bottomed flask at ambient temperature was added sulfuryl chloride (0.46 ml, 5.7 mmol) and the mixture was stirred at ambient temperature for 2 hr. Additional sulfuryl chloride was added (0.15 ml, 1.87 mmol) and the reaction mixture was stirred for 12 hr. The reaction mixture was transferred to a separatory funnel and washed with water (3×50 ml). The organic phase was dried over anhydrous sodium sulfate and concentrated to give a pale yellow solid (1.16 g, 97%).

$^1$H NMR (300 MHz, $CDCl_3$) δ 8.05 (d, J=9.0 Hz, 1H), 7.37 (d, J=9.2 Hz, 1H), 6.07 (s, 1H).

MS m/z 209, 211 (M-H).

2'-(7-Chloro-6-hydroxybenzothiazol-2-yl)-benzothiazole-6'-acetic acid (FIG. 1h). To a 100-ml round-bottomed flask was added 2-aminobenzothiazole-6-acetic acid (0.72 g, 3.46 mmol) and 50% aqueous potassium hydroxide solution. The flask was fitted with a reflux condenser and the reaction mixture was heated at 100–105° C. for 2 hr using an oil bath. The reaction was cooled in an ice bath, diluted with 5.0 ml of water and then neutralized to pH 6 by addition of glacial acetic acid. To the resulting mixture was added all at once a solution of 7-chloro-2-cyano-6-hydroxybenzothiazole (0.36 g, 1.73 mmol) in methanol (20 ml). A yellow precipitate formed immediately. The reaction mixture was stirred at ambient temperature for 12 hr. The precipitate was isolated by filtration and washed with acetone. The solid material was air dried and then dried under vacuum to provide 0.28 g (43%) of the desired product as tan-colored flakes.

$^1$H NMR (300 MHz, DMSO-$d_6$) δ 7.93 (d, J=8.4 Hz, 1H), 7.72 (s, 1H), 7.43 (d, J=7.9 Hz, 2H), 6.75 (d, J=8.8 Hz, 1H), 3.57 (s, 2H).

MS m/z 375, 377 (M-H).

EXAMPLE 8

FBBT Synthesis

2-Cyano-7-fluoro-6-hydroxybenzothiazole. To a suspension of 2-cyano-6-hydroxybenzothiazole (2.0 g, 11.4 mmol) in dichloromethane (50 ml) in a 250-ml round-bottomed flask was added 3,5-dichloro-1-fluoropyridinium triflate (6.1 g, 19.3 mmol). The reaction flask was fitted with a reflux condenser and the mixture was brought to reflux under argon atmosphere for 53 hr. Additional 3,5-dichloro-1-fluoropydidinium toiflate was added (1.0 g, 3.2 mmol) and reaction continued for another 22 hr. Additional 3,5-dichloro-1-fluoropylidinium triflate was added (1.0 g, 3.2 mmol) and reaction continued for another 27 hr. Additional 3,5-dichloro-1-fluoropyridinium triflate was again added (1.0 g, 3.2 mmol) and reaction continued for another 72 hr. The reaction mixture was concentrated by rotoevaporation to give a brown residue that was purified by flash chromatography with 100 g of silica gel and methylene chloride as eluting solvent. The title compound was obtained as a white solid. Yield: 0.97 g (44%).

$^1$H NMR (300 MHz, $CDCl_3$) δ 7.94 (d, J=8.8 Hz, 1H), 7.37 (t, J=8.7 Hz, 1H);

$^{19}$F NMR (282 MHz, $CDCl_3$) δ-138.83;

MS (ESI-) m/z 193 (M-H).

Figure 1B:
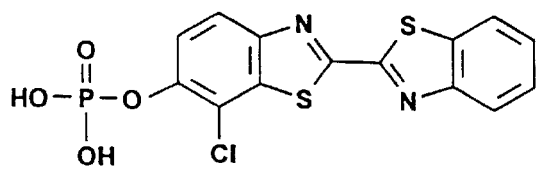
Figure 1B:
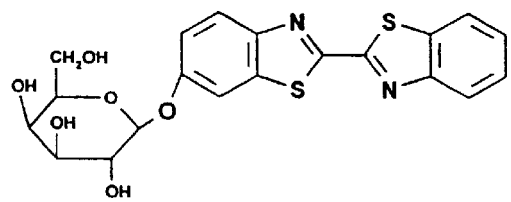
Figure 1B:
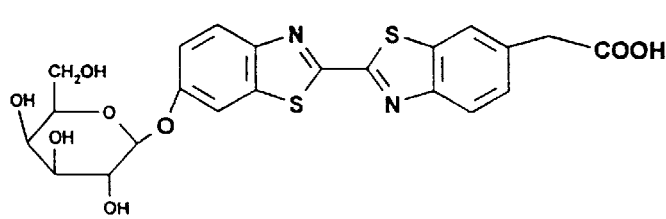
Figure 1B:
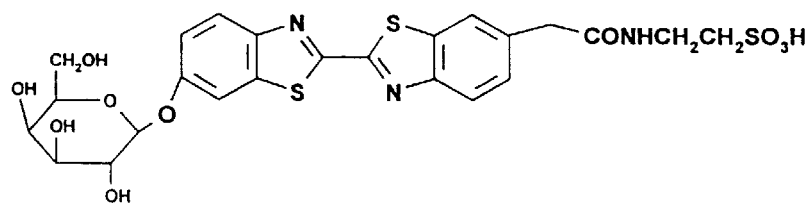
Figure 1B:
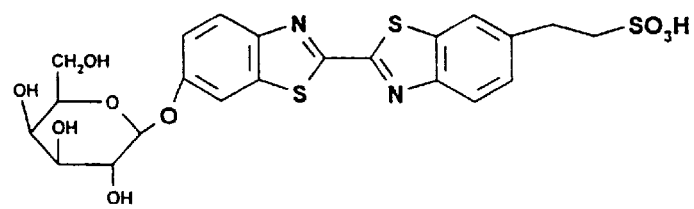
Figure 1B:
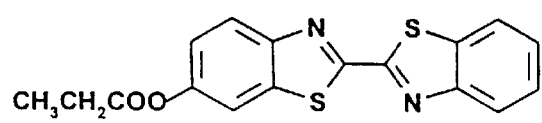
Figure 1B:
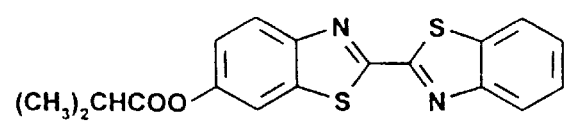

2'-(2-Benzothiazolyl)-7'-fluoro-6'-hydroxybenzothiazole (FIG. 1a). To a solution of 2-cyano-7-fluoro-6-hydroxybenzothiazole (0.43 g, 2.2 mmol) in methanol (5 ml) and water (2 ml) was added 2-aminothrophenol (0.36 ml, 3.3 mmol) and the mixture was stirred at ambient temperature for 12 hr. The yellow precipitate was isolated by filtration and washed with acetone. The yellow solid material was air-dried and then dried under vacuum to afford 0.45 g (67%) of the title compound.

$^1$H NMR (300 MHz, DMSO-$d_6$) δ 10.72 (br s, 1H), 8.22 (d, J=8.6 Hz, 1H), 8.16 (d, J=7.6 Hz, 1H), 7.88 (d, J=8.9 Hz, 1H), 7.59 (m, 2H), 7.29 (t, J=8.8 Hz, 1H);

$^{19}$F NMR (282 MHz, DMSO-$d_6$) δ-135.10;

MS (ESI-) m/z 301 (M-H).

EXAMPLE 9

Synthesis of BEBO

Synthesis of 2'-(2-Benzoxazolyiethenyl)-6'-hydroxybenzothiazole (FIG. 2a): A mixture of 6-methoxybenzothiazole-2-aldehyde (100 mg, 0.7 mmol), 2-methylbenzoxazole (0.5 ml) and zinc chloride (100 g) was heated at 180° C. under argon for 10 min and then cooled down to room temperature. Methanol (7 ml) was added. The resulting precipitate was collected, washed with methanol and dried in vacuum. The dried material was dissolved in chloroform (5 ml). Boron tribromide (0.3 ml) was added. The reaction mixture was stirred at room temperature for 4 hr and then diluted with a heptane (10 ml). The precipitate was filtered, washed with 5% ammonium hydroxide aqueous solution, and then dried. The crude product was purified by silica gel column chromatography. Yield: 44 mg (29%).

$^1$H NMR (300 MHz, DMSO-$d_6$): δ 7.95 (1H, d), 7.90 (1H, d), 7.80 (2H, m), 7.50–7.40 (4H, m), 7.04 (1H, dd).

EXAMPLE 10

Enzymatic Activity Tests (1) Alkaline Phosphatase: 1 mg BEBTP was dissolved in 10 ml AttoPhos buffer (JBL Scientific, San Luis Obispo,

--- mixture was stirred at room temperature for 90 min and then poured into 200 ml methyl b-butyl ether. The resulting precipitate was filtered and dried in vacuum. Yield: 1.3 g.

MS: m/z 439 (M-).

Calif.). A small quantity of alkaline phosphatase (Calf Intestine, Calzyme, San Luis Obispo, Calif.) was added. An orange red fluorescence was quickly developed.

(2) β-Galactosidase: 1 mg BEBTESG was dissolved in 10 ml 0.1 M potassium phosphate buffer (pH 7) containing 10 mM DTT and 1 mM $MgCl_2$ and a small quantity of β-galactosidase (Cat. No. 104939, *E. Coli*, ICN Biomedicals, Inc.) was added. An orange red fluorescence was quickly developed.

(3) Esterase and Lipase:

Buffer: 100 mM Tris. HCl, pH 8.0.

Substrate Stock Solution: 2 mM acyl BBT dioxane solution.

Enzymes: All enzymes were from Sigma: Esterase from Porcine Liver(E3 128); Lipase from Pseudomonas species (L9518); Lipase from Candida cylindracea (L1754). Dilute the enzyme by the buffer to the desired concentration before use.

Instrument: Squoia-Tumer Fluorometer, Model 450. Excitation at 440 nm and Emission at 550 nm.

Figure 4:
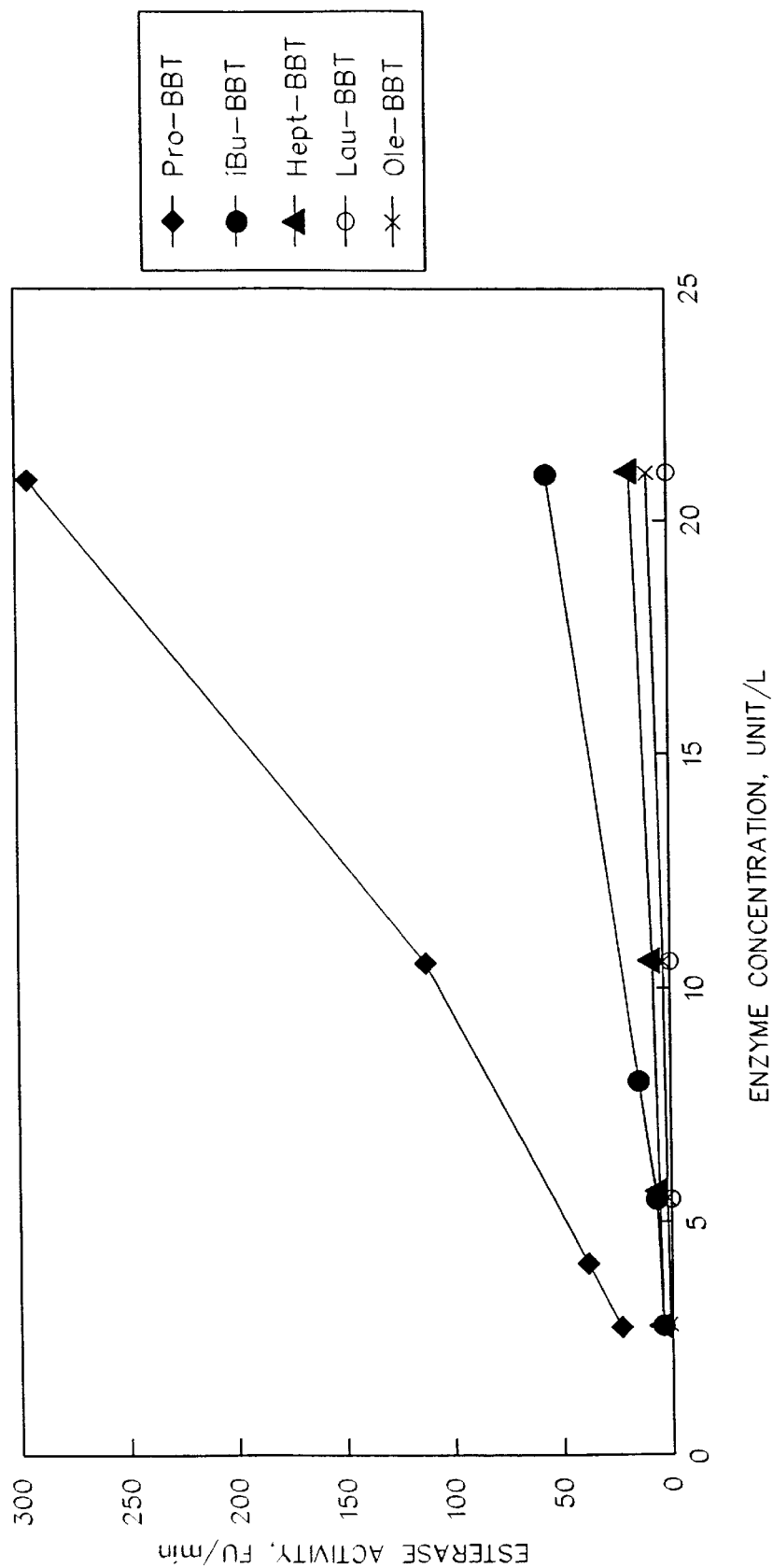
FIG. 4 shows the activity of porcine liver esterase towards BBT acyl derivatives.
Figure 5:
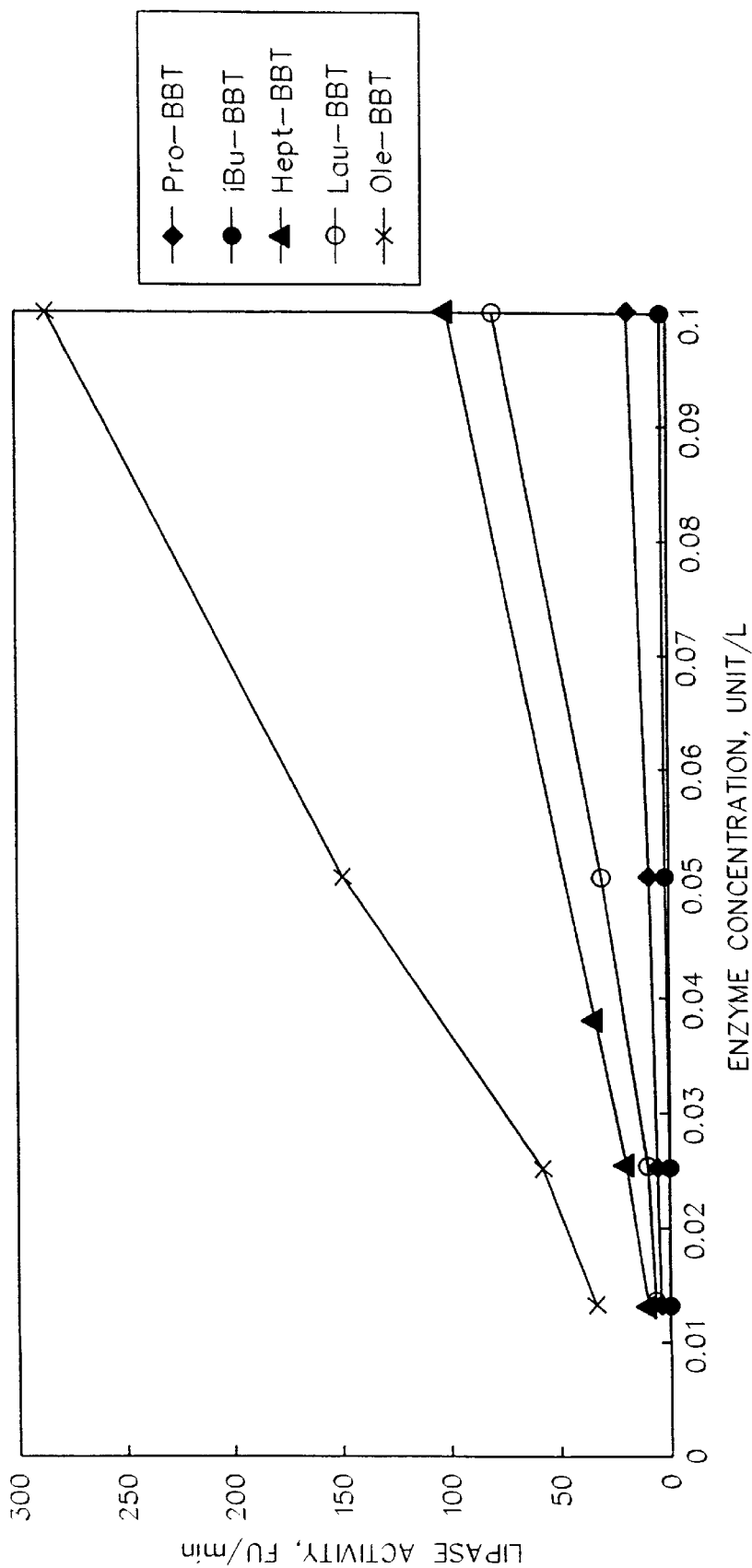
FIG. 5 shows the activity of Pseudomonas species lipase towards BBT acyl derivatives.
Figure 6:
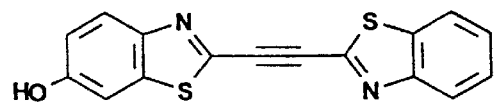
FIG. 6: shows representative chemical structures of dibenzazole compounds where n=1 and Z is —C≡C—.

Procedure:

1. Set the Fluorometer Gain to 200.
2. Set the Fluorometer Zero to 0 with the Tris buffer.
3. Set the Fluorometer Span to 1000 using JBL 10 ng BBT (FEY) standard solution.
4. Pipette 980 µl buffer to a glass test tube (Baxter, Cat. No. T1290–3).
5. Add 10 µl substrate stock solution and mix well.
6. Measure and record the blank reading.
7. Add 10 µl enzyme solution.
8. Take fluorescence reading every one minute for 3 minutes and record.
9. Calculate the fluorescence unit change (FU/min) by subtracting the first-minute reading from the second-minute reading.
10. Plot FU/min vs. enzyme concentration, u/L (FIG. 4 and FIG. 5).

The enzymatic activity of these newly synthesized acetyl BBT compounds towards both lipase and esterase showed that, on hydrolysis by the enzymes, these substrates yielded fluorescence with high sensitivity in a very short time. However, these new substrates also showed great selectivity between lipase and esterase, especially for propionyl BBT and oleoyl BBT. Propionyl BBT is a very effective substrate for porcine liver esterase but a very poor substrate for lipases. Conversely, oleoyl BBT showed high activity for lipases from Pseudomonas but low activity for the esterase (FIG. 4 and FIG. 5).

EXAMPLE 11

Oligonucleotide Labeling (1) Labeled Oligonucleotide Synthesis: 2'-(2-Acetoxybenzothiazolyl)-6'-benzothiazolylethyl phosphoramidite was incorporated into the 5'-end of oligonucleotides using the standard automated DNA synthesis method on a DNA synthesizer. The following sequence (BBTE-TCTCCCAGCGTGCGCCAT; SEQ ID NO: 1) is a labeled example:

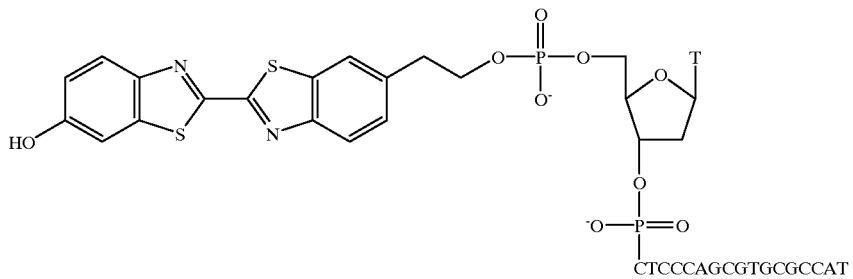

(2) Labeled Oligonucleotide HPLC Analysis: The labeled oligonucleotide was analyzed by a DIONEX Nucleopac (PA-100) analytical HPLC anion-exchange column. The labeled sequence shown above has a retention time 9.62 min while the unlabeled same sequence has retention time 9.10.

(3) UV Spectrum: The UV spectrum of the labeled oligonucleotide showed a 385 nm maximum absorbance peak which is typical for 2'-(2-hydroxybenzothiazolyl)-6'-benzothiazole structure while the non-labeled same oligo-nucleotide did not show this peak at that wavelength.

(4) Fluorescence: The labeled BBTE-TCTCCCAGCGTGCGCCAT (SEQ ID NO: 1) was separated on a standard DNA electrophoresis gel, along with the non-labeled TCTCCCAGCGTGCGCCAT (SEQ ID NO: 1). The labeled oligonucleotide showed a strong yellow fluorescent band on the gel while the non-labeled did not.

EXAMPLE 12

Protein Labeling

Test of 2'-(2-Hydroxybenzothiazolyl)-benzothiazole-6-acetic acid N-Hydroxysuccinimide Ester for Labeling Amino-Containing Materials: 2'-(2—Hydroxybenzothiazolyl)-benzothiazole-6-acetic acid N-hydroxysuccinimide ester (1.3 g, 3.0 mmol) was dissolved in DMF (7 ml). Taurine (2.0 g, 5.3 mmol) was dissolved in water (10 ml) at pH 10. The two solutions were combined and the reaction mixture was stirred at room temperature overnight. The solution was neutralized with 6 N HCl to pH 7–8 and then concentrated to dryness. The residue was dissolved in water and purified by Cl8 column chromatography. Yield: 0.5 g.

MS: m/z 448 (M⁻).

Test of 2'-(2-Hydroxybenzothiazolyl)-benzothiazole-6-acetic acid N-Hydroxysuccinimide Ester for Labeling Protein: Bovine serum albumin (BSA, 5 mg) was dissolved in water (0.5 ml) and 2'-(2-Hydroxybenzothiazolyl)-benzothiazole-6-acetic acid N-Hydroxysuccinimide Ester DMF solution (10 mg in 0.1 ml) was added. pH of the reaction mixture was adjusted with saturated sodium carbonate to 9–10. After stirring for 30 min at room temperature, a sample of the labeled BSA was analyzed on standard SDS-PAGE gel electrophoresis, along with a non-labeled BSA sample. The labeled BSA lane showed characteristic 2'-(2-Hydroxybenzothiazolyl)-benzothiazole fluorescence while the non-labeled BSA lane did not.

EXAMPLE 13

Detection of Analytes using Blotting Techniques
Western Blot Detection of Protein Analytes Using C1BBTP:
Electrophoresis buffer is a mixture of Tris buffered saline and SDS@pH 8.3. Electrotransfer buffer contains Tris, glycine and 20% methanol@pH 8.4. All blocking buffers and wash buffers contain Tris buffered saline, Tween-20 and Hammerstein Casein @ pH 7 (Lyophilized 3.0 mg C1BBTP with 250 mM TAPS and 4% D-manitol). Reconstitution ;buffer contains 500 mM DEA (diethanolamine)@pH 9, 1 mM $MgCl_2$, 1 mM $ZnCl_2$, 0.01%$NaN_3$. Final wash buffer is composed of 25–50 mM DEA@pH 9.

Procedures:
1. Prepare serial dilutions of protein analyte (e.g. β-galactosidase).
2. Electrophorese analyte across polyacrylamide gel.
3. Electrotransfer protein analytes from gel to a membrane (e.g PVDF).
4. Probe protein analyte on membrane with antibodies. Make sure at least one antibody or conjugate is labeled with Alkaline Phosphatase.
5. Incubate membrane with 2 ml of reconstituted 0.25 mMC1BBTP in 500 mM DEA@pH 9 (also contains 1 mM $MgCl_2$, 1 MM $ZnCl_2$, and 0.01% $NaN_3$) for 5 minutes.

Wash membrane with 25–50 mM DEA@pH 8 and visualize with UV light@365 nm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound having the structure:

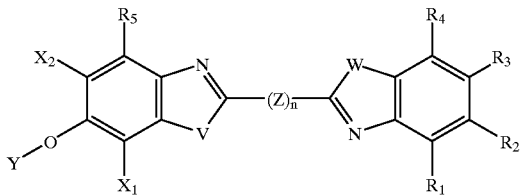

wherein, $R_1$, $R_2$, $R_3$, $R_4$, and $R_5$, are independently H or substituents which aid in solubility of the compound or which provides a linker arm for linking the compound to another moiety;

Y is H or a cleavable moiety;

$X_1$ and $X_2$ are separately and independently hydrogen, halogen, $CF_3$, or $SO_3H$ providing however that $X_1$ and $X_2$ are not concurrently hydrogen;

V and W are independently oxygen and sulfur;

Z is —C=C—, —C≡C—, or an aromatic ring moiety; and n is 0, 1, or 2.

2. A compound having the structure:

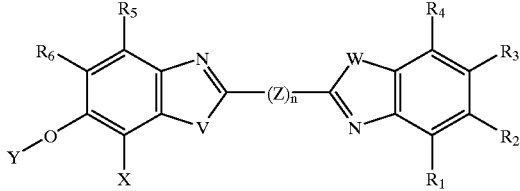

wherein, $R_1$, $R_2$, $R_3$, $R_4$, $R_5$, and $R_6$ are independently H or substituents which aid in solubility of the compound or which provides a linker arm for linking the compound to another moiety;

Y is H or a cleavable moiety;

---

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

TCTCCCAGCG TGCGCCAT                                                 18

X is halogen, $CF_3$, or $SO_3H$;

V and W are independently oxygen or sulfur;

Z is —C=C—, —C≡C— or an aromatic ring moiety; and n is 0, 1, or 2.

3. A compound according to claim 1 wherein $R_1$, $R_2$, $R_3$, $R_4$, or $R_5$ are H.

4. A compound according to claim 2 wherein $R_1$, $R_2$, $R_3$, $R_4$, $R_5$ or $R_6$ are H.

5. A compound according to claim 1 or 2 wherein $R_1$, $R_2$, $R_3$, $R_4$, and $R_5$ are separately and independently selected from —H, —$SO_3^-$ or —$CO_2^-$.

6. A compound according to claim 1 or 2 wherein $R_1$, $R_2$, $R_3$, $R_4$, and $R_5$ are separately and independently $PO_4^{-2}$ when Y is a cleavable moiety other than phosphoryl.

7. A compound according to claim 1 or 2 wherein $R_1$ and $R_2$, or $R_2$ and $R_3$, or $R_3$ and $R_4$ together form an aromatic ring.

8. A compound according to claim 7 wherein $R_1$ and $R_2$, or $R_2$ and $R_3$, or $R_3$ and $R_4$ together form benzene or naphthalene.

9. A compound according to claim 1 or 2 wherein at least one of $R_1$, $R_2$, $R_3$, $R_4$, and $R_5$ is —$CH_2CH_2SO_3H$.

10. A compound according to claim 1 or 2 wherein Y is a glycosyl moiety selected from the group consisting of galactosyl, glucosyl and glucuronosyl.

11. A compound according to claim 1 or 2 wherein Y is selected from the group consisting of galactosyl, glucosyl and glucuronosyl.

12. A compound according to claim 1 or 2 wherein Y is $R_8$—C(=O)— wherein $R_8$ is a straight chain or branched alkyl or alkenyl group of about 12 to about 24 carbon atoms.

13. A compound according to claim 10 wherein $R_8$ is a straight chain or branched alkyl or alkenyl group of about 16 to about 20 carbon atoms.

14. A compound according to claim 13 wherein $R_8$ is oleoyl.

15. A compound according to claim 1 or 2 wherein Y is $R_7$—C(=O)— wherein $R_7$ is a straight chain or branched alkyl or alkenyl group of 1 to about 12 carbon atoms.

16. A compound according to claim 15 wherein $R_7$ is a straight chain or branched alkyl or alkenyl group of 1 to about 5 carbon atoms.

17. A compound according to claim 15 wherein $R_7$ is heptanoyl, lauroyl, propionyl, or iso-butyryl.

18. A compound according to claim 1 or 2 wherein X is independently F or Cl.

19. A compound according to claim 1 or 2 wherein Z is an aromatic ring moiety selected from the group consisting of benzene, pyrrole, pyridine, furan and thiophene.

Figure 1C:
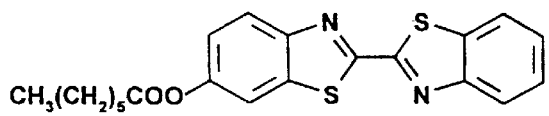
Figure 1C:
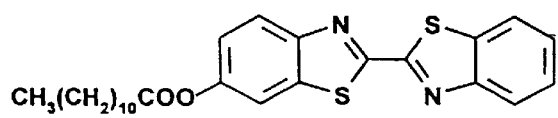
Figure 1C:
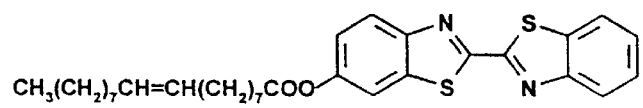
Figure 1C:
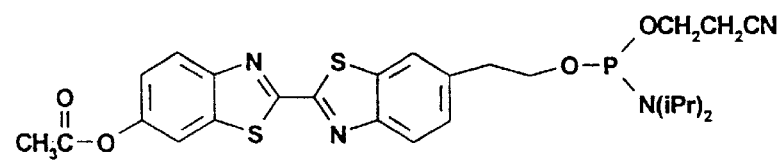
Figure 1C:
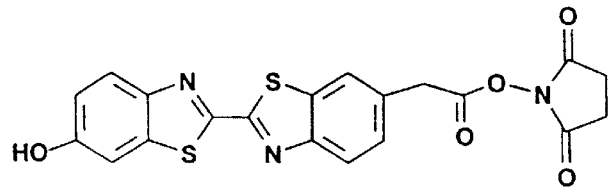
Figure 1C:
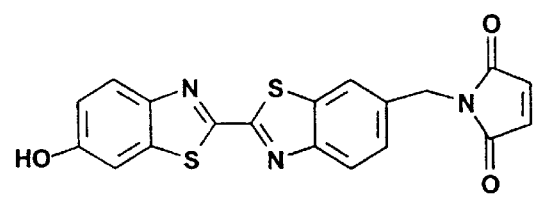
Figure 1C:
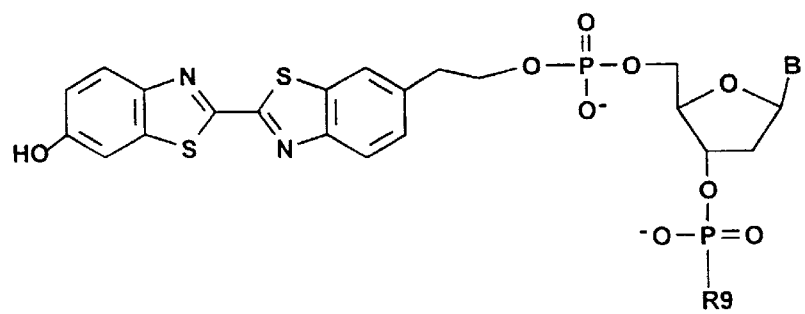

20. A compound having the structure according to any of the Structures listed in FIGS. 1A, 1B, or 1C.

21. A compound having the structure according to any of the Structures listed in FIGS. 2A or 2B.

22. A compound according to claim 1 or 2 further comprising a linker arm substituted for at least one of $R_1$, $R_2$, $R_3$, or $R_4$.

23. A compound according to claim 22 wherein the linker arm is of the formula —$(CH_2)_n$—$R_{10}$ wherein n is a number selected from 0, 1, 2, 3, 4 and 5 and $R_{10}$ is selected from the groups consisting of —OH, —$SO_3H$, —COOH, —C(=O)NH$(CH_2)_m R_{11}$, —O—P(O$CH_2CH_2CN$)(N($R_9$)$_2$),

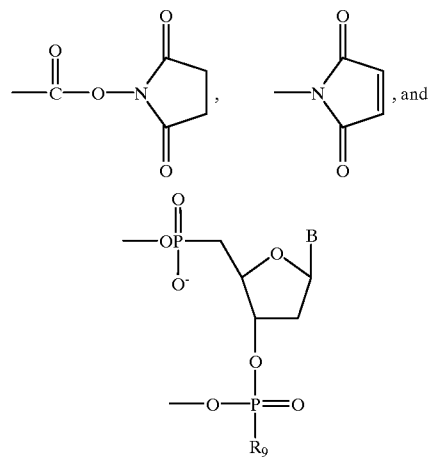

wherein $R_{11}$, is selected from the group consisting of —OH, $SO_3H$ and —COOH, m is a number selected from 1, 2, 3, 4 and 5, $R_9$ is an alkyl group of 1 to about 6 carbon atoms and B is a purine or pyrimidine moiety.

24. A compound according to claim 1 or 2 conjugated to a peptide, oligopeptide, polypeptide, protein, nucleoside, oligonucleotide, polynucleotide, DNA, RNA, or biotin.

25. A method of detecting an agent in a sample, comprising:

(a) isolating an agent from a sample by gel electrophoresis;

(b) transferring the isolated agent to a membrane;

(c) adding an agent binding ligand to the isolated agent on the membrane, wherein the agent binding ligand is conjugated to a compound according to claim 1 or 2;

(d) incubating the agent binding ligand with the membrane under conditions and for a time to allow the agent binding ligand to bind the agent; and (e) detecting the presence of the compound by fluorescence.

26. A method according to claim 25 wherein the agent is a protein, RNA or DNA.

27. A method of detecting an agent in a sample, comprising:

(a) adding a compound according to claim 1 or claim 2 to a sample; and (b) detecting the presence of the compound by fluorescence.

28. A method for the detection of two or more agents simultaneously in a sample, comprising:

(a) adding two or more compounds according to claim 1 or 2 which are conjugated to two or more agent binding ligands which bind the agents being detected; and (b) detecting the presence of each compound by fluorescence.

29. A compound having the structure:

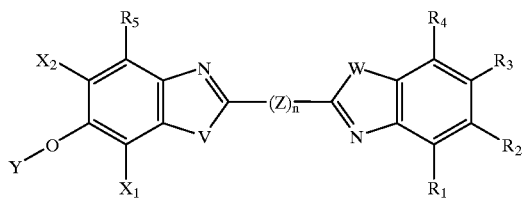

wherein, $R_1$, $R_2$, $R_3$, $R_4$, and $R_5$, are independently H or substituents which aid in solubility of the compound or which provide a linker arm for linking the compound to another moiety;

Y is H or a cleavable moiety;

X, and $X_2$ are separately and independently hydrogen, halogen, $CF_3$, or $SO_3H$;

V and W are independently oxygen or sulfur;

Z is —C=C—, —C≡C— or an aromatic ring moiety; and n is 1, or 2.

30. A compound according to claim 29 wherein $X_1$ is halogen and $X_2$ is hydrogen.

31. A compound having the structure:

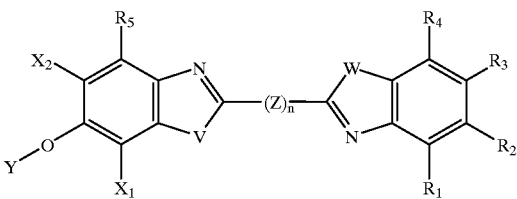

wherein, $R_1$, $R_2$, $R_3$, $R_4$, and $R_5$, are independently H or substituents which aid in solubility of the compound and at least one of $R_1$, $R_2$, $R_3$, or $R_4$ provide a linker arm for linking the compound to another moiety;

Y is H or a cleavable moiety;

$X_1$ and $X_2$ are separately and independently hydrogen, halogen, $CF_3$, or $SO_3H$;

V and W are separately and independently oxygen and sulfur;

Z is —C=C—, —C≡C—, or an aromatic ring moiety; and n is 0, 1, or 2.

32. A compound according to claim 31 wherein $X_1$ is halogen and $X_2$ is hydrogen.

* * * * *